US010227366B2

(12) United States Patent
Cysewski et al.

(10) Patent No.: US 10,227,366 B2
(45) Date of Patent: Mar. 12, 2019

(54) BIS-IRIDIUM-COMPLEXES FOR MANUFACTURING OF ECL-LABELS

(71) Applicant: Roche Diagnostics Operations, Inc., Indianapolis, IN (US)

(72) Inventors: Robert Cysewski, Chojnice (PL); Luisa de Cola, Strasbourg (FR); Jesus Miguel Fernandez Hernandez, Murcia (ES); Hans-Peter Josel, Weilheim (DE); Elena Longhi, Lecco (IT); Gaston Hubertus Maria Vondenhoff, Penzberg (DE)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 0 days.

(21) Appl. No.: 14/610,110

(22) Filed: Jan. 30, 2015

(65) Prior Publication Data
US 2015/0148536 A1 May 28, 2015

Related U.S. Application Data

(63) Continuation of application No. PCT/EP2013/002324, filed on Aug. 2, 2013.

(30) Foreign Application Priority Data

Aug. 2, 2012 (EP) .................................. 12179056

(51) Int. Cl.
| C07F 15/00 | (2006.01) |
| G01N 33/533 | (2006.01) |
| H01L 51/00 | (2006.01) |
| C09K 11/06 | (2006.01) |
| G01N 33/58 | (2006.01) |
| H01L 51/50 | (2006.01) |

(52) U.S. Cl.
CPC .......... *C07F 15/0033* (2013.01); *C09K 11/06* (2013.01); *G01N 33/533* (2013.01); *G01N 33/582* (2013.01); *H01L 51/009* (2013.01); *H01L 51/0085* (2013.01); *C09K 2211/1007* (2013.01); *C09K 2211/1029* (2013.01); *C09K 2211/185* (2013.01); *G01N 2458/30* (2013.01); *H01L 51/5012* (2013.01)

(58) Field of Classification Search
CPC .................................................. C07F 15/0033
USPC ............................................................. 546/4
See application file for complete search history.

(56) References Cited

U.S. PATENT DOCUMENTS

| 5,219,847 | A | 6/1993 | Taguchi et al. |
| 7,067,202 | B2 | 6/2006 | Fujii |
| 8,772,486 | B2 * | 7/2014 | Cysewski ........... C07F 15/0033 546/4 |
| 8,836,637 | B2 * | 9/2014 | Bychkov ............... G06F 1/1626 345/156 |
| 2004/0091738 | A1 | 5/2004 | Psai et al. |
| 2004/0239237 | A1 | 12/2004 | Matsusue et al. |
| 2006/0063630 | A1 | 3/2006 | Jurado |
| 2006/0134461 | A1 | 6/2006 | Huo et al. |
| 2006/0237714 | A1 | 10/2006 | Park et al. |
| 2006/0263630 | A1 | 11/2006 | Ho et al. |
| 2007/0015005 | A1 | 1/2007 | Chen et al. |
| 2007/0087221 | A1 | 4/2007 | Wu et al. |
| 2007/0141394 | A1 | 6/2007 | Cheng et al. |
| 2008/0217606 | A1 | 9/2008 | Cheng et al. |
| 2008/0299414 | A1 | 12/2008 | Watanabe et al. |
| 2009/0209048 | A1 | 8/2009 | Kwon et al. |
| 2010/0252433 | A1 | 10/2010 | Dratz et al. |
| 2013/0323719 | A1 | 12/2013 | Cysewski et al. |
| 2013/0323857 | A1 | 12/2013 | Cysewski et al. |
| 2015/0140682 | A1 | 5/2015 | Bergmann et al. |

FOREIGN PATENT DOCUMENTS

| CN | 1397559 A | 2/2003 |
| CN | 1474826 A | 2/2004 |
| CN | 101750486 A | 6/2010 |
| CN | 102004099 A | 4/2011 |
| CN | 102168104 A | 8/2011 |
| CN | 102503993 A | 6/2012 |
| CN | 102604628 A | 7/2012 |
| DE | 102008063490 A1 | 6/2010 |
| EP | 0404097 A2 | 12/1990 |
| EP | 1418217 A1 | 5/2004 |
| EP | 2062959 A2 | 5/2009 |
| JP | 2007-080593 A | 3/2007 |
| JP | 2007169474 A2 | 5/2007 |
| WO | 1987/006706 A1 | 11/1987 |
| WO | 199301161 A1 | 1/1993 |
| WO | 2003/002974 A2 | 1/2003 |
| WO | 03063555 A1 | 7/2003 |
| WO | 2005019373 A2 | 3/2005 |
| WO | 2005118606 A1 | 12/2005 |
| WO | 2006/115301 A1 | 11/2006 |

(Continued)

OTHER PUBLICATIONS

Dorwald F. A. Side Reactions in Organic Synthesis, 2005, Wiley: VCH, Weinheim p. IX of Preface p. 1-15.*
Chin, Organometallics 2002, 21, 1739-1742.*
International Search Report dated Sep. 30, 2013 in Application No. PCT/EP2013/002324, 2 pages.
Altuntas, Esra et al., "Determination of the relative ligand-binding strengths in heteroleptic Ir(III) complexes by ESI-Q-TOF tandem mass spectrometry," Journal of Mass Spectrometry, 2012, pp. 34-40, vol. 47, No. 1.

(Continued)

*Primary Examiner* — Nizal S Chandrakumar
(74) *Attorney, Agent, or Firm* — Roche Diagnostics Operations, Inc.

(57) ABSTRACT

The present invention relates to novel bis-iridium-based Ir(III) complexes, labels manufactured using these complexes and a method for producing such complexes.

2 Claims, No Drawings

(56) References Cited

FOREIGN PATENT DOCUMENTS

| WO | 2007095118 A2 | 8/2007 |
|---|---|---|
| WO | 2008096609 A1 | 8/2008 |
| WO | 2009026235 A2 | 2/2009 |
| WO | 2009050281 A1 | 4/2009 |
| WO | 2010069442 A1 | 6/2010 |
| WO | 2010069444 A1 | 6/2010 |
| WO | 2010/074087 A1 | 7/2010 |
| WO | 2011000616 A1 | 1/2011 |
| WO | 2011/013685 A1 | 2/2011 |
| WO | 2011067401 A1 | 6/2011 |
| WO | 2011/134013 A1 | 11/2011 |
| WO | 2012/066686 A1 | 5/2012 |
| WO | 2012/079741 A1 | 6/2012 |
| WO | 2012/107419 A1 | 8/2012 |
| WO | 2012/107420 A1 | 8/2012 |

OTHER PUBLICATIONS

Cymerman, J. and Short, W. F., "150. Amidines. Part XII. Preparation of 9-substituted Phenanthridines from N-2-Diphenylylamidines," Journal of the American Chemical Society, 1949, pp. 703-707.

Kohmoto, Shigeo et al., "Room-Temperature Discotic Nematic Liquid Crystals over a Wide Temperature Range: Alkali-Metal-Ion-Induced Phase Transition from Discotic Nematic to Columnar Phases," Journal of the American Chemical Society, 2007, pp. 13364-13365, vol. 129.

Lion, C. et al., "Synthesis in the Phenanthridine Series, I. Search for Optimum Experimental Conditions in the Preparation fo 6-Alkylphenanthridines and of the Salt Thereof," Bulletin des Sociétés Chimiques Belges, 1989, pp. 557-566, vol. 99, with English translation.

Nicolai, Eric et al., "Synthesis and Angiotension II Receptor Antagonist Activity of C-Linked Pyrazole Derivatives," Chemical and Pharmaceutical Bulletin, 1994, pp. 1617-1630, vol. 42, No. 8, Pharmaceutical Society of Japan.

Nonoyama, Matsuo, "Chelating C-metallation of N-Phenylpyrazole with Rhodium(III) and Iridium(III)," Journal of Organometallic Chemistry, 1975, pp. 263-267, vol. 86.

Youn, So Won and Bihn, Joon Hyung, "Trifluoroacetic acid-mediated facile construction of 6-substituted phenanthridines," Tetrahedron Letters, 2009, pp. 4598-4601, vol. 50.

Hilpert, Hans, 118. Syntheses von 3-(2-Carboxy-4-pyridl)-und 3-(6-Carboxy-3-pyridl)-DL-alanin, Helvetica Chimica Acta, 1987, pp. 1307-1311, vol. 70.

Holliger, P., "Diabodies": Small bivalent and bispecific antibody fragments, Proc. Natl. Acad. Sci. USA, 1993, 6444-6448, 90.

Hudson, P.J. et al., Engineered antibodies, Nature Medicine, 2003, 129-134, 9 (1).

Lamansky et al., Synthesis and Characterization of Phosphorescent, Inorganic Chemistry, 2001, 1704-1711, 40, 1704-1711.

Lee, Young Hee et al., Theoretical Study of Ir(III) Complexes of Fluorinated Phenylbenzoquinoline as Red Phosphorescent Material, Japanese Journal of Applied Physics, 2006, pp. 563-567, vol. 45, No. 1B.

Moderhack, Dietrich and Schneider, Jan-Christoph, A New Series of Non-classical Type C Heteropentalenes: 2H-Pyrrolo[2,1-c][1,2,4]triazoles, Journal of Heterocyclic Chemistry, 2007, pp. 393-401, vol. 44, No. 2.

Plückthun, A., Antibodies from *Escherichia coli*, The Pharmacology of Monoclonal Antibodies, 1994, 269-315, 113.

LO, Kenneth Kam-Wing et al., Novel Luminescent Cyclometalated Iridium(III) Diimine Complexes That Contain a Biotin Moiety, Organometallics, 2004, pp. 3108-3116, vol. 23.

Liu, Chenchen et al., NMR study on iridium(iii) complexes for identifying disulfonate substituted bathophenanthroline regioisomers, Magnetic Resonance in Chemistry, 2011, pp. 816-823, vol. 49.

Vavarro-Ranninger, Carmel et al., A cyclometallated Pd(II) complex containing a cytosine model nucleobase, Journal of Organometallic Chemistry, 1998, pp. 103-110, vol. 558.

Ragni, Roberta et al., Iridium(III) Complexes with Sulfonyl and Fluorine Substituents: Synthesis, Stereochemistry and Effect of Functionalisation on their Photophysical Properties, Chemistry A European Journal, 2009, pp. 136-148, vol. 15.

* cited by examiner

BIS-IRIDIUM-COMPLEXES FOR MANUFACTURING OF ECL-LABELS

CROSS REFERENCE TO RELATED APPLICATIONS

This application is a continuation of PCT/EP2013/002324 filed Aug. 2, 2013 and claims priority to EP Patent Application No. 12179056.2 filed Aug. 2, 2012, the disclosures of which are hereby incorporated by reference in their entirety.

BACKGROUND OF THE INVENTION

The present invention relates to novel bis-iridium-complexes and their use in the manufacturing of luminescent labels, especially electrochemiluminescent labels, as well as to a method for producing ECL-labels based on such bis-iridium-complexes.

Electrogenerated chemiluminescence (also called electrochemiluminescence and abbreviated ECL) is the process whereby species generated at electrodes undergo high-energy electron-transfer reactions to form excited states that emit light. The first detailed ECL studies were described by Hercules and Bard et al. in the mid-1960s. After about 50 years of study, ECL has now become a very powerful analytical technique and is widely used in the areas of, for example, immunoassay, food and water testing, and biowarfare agent detection.

There is a tremendous number of compounds that appears to be of interest for use in organic light emitting devices (OLEDs). These compounds are appropriate for use in solid materials or may be dissolved in organic fluids. However, no conclusion can be drawn regarding their utility in an aqueous medium as e.g., required for detection of an analyte from a biological sample.

In general ECL-based detection methods are based on the use of water-soluble ruthenium complexes, comprising Ru(II+) as metal ion.

Despite significant improvements made over the past decades, still a tremendous need exists for more sensitive electrochemiluminescence-based in vitro diagnostic assays.

It has now been surprisingly found that certain iridium-based Ir(III+) luminescent complexes, represent very promising labels for future high sensitive ECL-based detection methods and that novel bis-iridium-complexes, as disclosed herein below, can be used with great advantage to manufacture such ECL-labels.

SUMMARY OF THE INVENTION

The present invention discloses an iridium-based chemiluminescent compound of Formula I

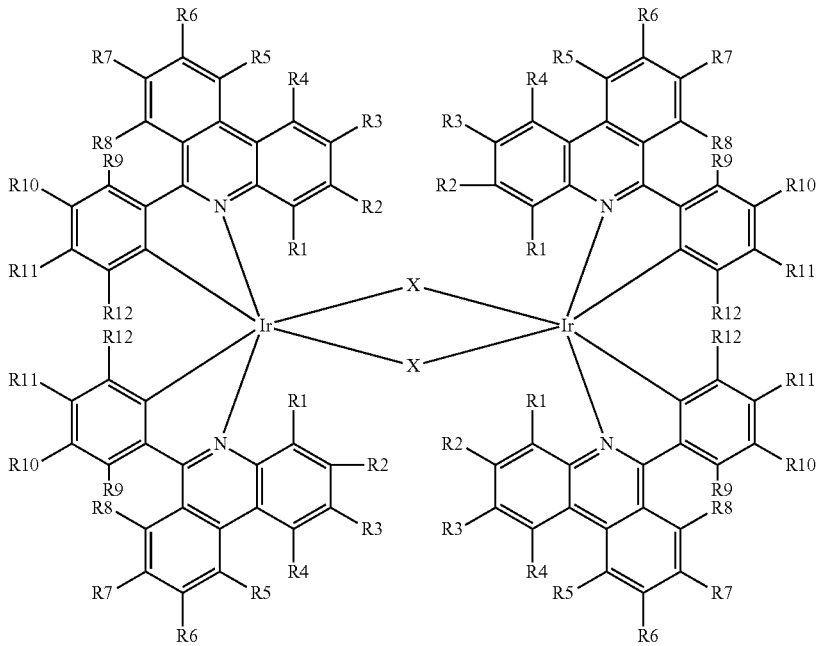

wherein each X is independently chloro, bromo, iodo, hydroxyl, methoxy, ethoxy, phenoxy, cyanato or diphenylphosphanyl, wherein each R1-R12 independently is hydrogen, halide, cyano- or nitro-group, amino, substituted amino, alkylamino, substituted alkylamino, arylamino, substituted arylamino, alkylammonium, substituted alkylammonium, carboxy, carboxylate, carboxylic acid ester, carbamoyl, hydroxy, substituted or unsubstituted alkyloxy, substituted or unsubstituted aryloxy, sulfanyl, substituted or unsubstituted alkylsulfonyl, substituted or unsubstituted arylsulfonyl, sulfo, sulfino, sulfeno, sulfonate, sulfinate, sulfenate, sulfamoyl, sulfoxide, phosphono, hydroxyphosphinoyl, hydroxy-alkyl-phosphinoyl, phosphonate, phosphinate or R13, wherein R13 is aryl, substituted aryl, alkyl, substituted alkyl, branched alkyl, substituted branched alkyl, arylalkyl, substituted arylalkyl, alkylaryl, substituted alkylaryl, alkenyl, substituted alkenyl, alkynyl, substituted alkynyl, amino-alkyl, substituted amino-alkyl, amino-alkoxy, substituted amino-alkoxy, amino-aryl, substituted amino-aryl, amino-aryloxy, substituted amino-aryloxy, wherein within R1-R12 two adjacent Rs can form an aromatic ring or a substituted aromatic ring, wherein the substituent is selected from hydrogen, alkyl, substituted alkyl, halide, cyano- or nitro-group, a hydrophilic group, like amino, substituted amino, alkylamino, substituted alkylamino, alkylammonium, substituted alkylammonium, carboxy, carboxylate, carboxylic acid ester, carbamoyl, hydroxy, substituted or unsubstituted alkyloxy, substituted or unsubstituted aryloxy, sulfanyl, substituted or unsubstituted alkylsulfonyl, substituted or unsubstituted arylsulfonyl, sulfo, sulfino, sulfeno, sulfonate, sulfinate, sulfenate, sulfamoyl, sulfoxide, phosphono, hydroxyphosphinoyl, hydroxyl-alkyl-phosphinoyl, phosphonate, phosphinate or, wherein within R1-R12 two adjacent Rs can form an aliphatic ring or a substituted aliphatic ring, wherein the substituent is selected from hydrogen, alkyl, substituted alkyl, halide, cyano- or nitro-group, a hydrophilic group, like amino, substituted amino, alkylamino, substituted alkylamino, alkylammonium, substituted alkylammonium, carboxy, carboxylate, carboxylic acid ester, carbamoyl, hydroxy, substituted or unsubstituted alkyloxy, substituted or unsubstituted aryloxy, sulfanyl, substituted or unsubstituted alkylsulfonyl, substituted or unsubstituted arylsulfonyl, sulfo, sulfino, sulfeno, sulfonate, sulfinate, sulfenate, sulfamoyl, sulfoxide, phosphono, hydroxyphosphinoyl, hydroxyl-alkyl-phosphinoyl, phosphonate, phosphinate, wherein, if in any of R1-R13 a substitution is present, the substituent in R1-R13 is each independently selected from a halide, cyano- or nitro-group, a hydrophilic group, like an amino, alkylamino, alkylammonium, carboxy, carboxylate, carboxylic acid ester, carbamoyl, hydroxy, alkyloxy, arylalkyloxy, aryloxy, alkylaryloxy, polyethylenoxy, polypropylenoxy, sulfanyl, alkylsulfonyl, arylsulfonyl, sulfo, sulfino, sulfeno, sulfonate, sulfinate, sulfenate, sulfamoyl, sulfoxide, phosphono, hydroxyphosphinoyl, hydroxyl-alkyl-phosphinoyl, phosphonate, phosphinate, wherein alkyl is a linear or branched alkyl chain with a length of 1-20 carbon atoms or a heteroalkyl chain with the length of 1-20 atoms comprising 1-4 heteroatoms selected from O, N, P, and S, wherein aryl is a 5, 6, or 7 member aryl ring system, or a 5, 6, or 7 member heteroaryl ring system comprising 1-3 heteroatoms selected from O, S and N, with the proviso that at least one of R1-R12 is sulfo-alkyl, sulfo-aryl, sulfo-alkoxy, sulfo-aryloxy, sulfo, sulfino-alkyl, sulfino-aryl, sulfino-alkoxy, sulfino-aryloxy, sulfino, sulfeno-alkyl, sulfeno-aryl, sulfeno-alkoxy, sulfeno-aryloxy, sulfeno, sulfamoyl-alkyl, sulfamoyl-aryl, sulfamoyl-alkoxy, sulfamoyl-aryloxy, sulfamoyl, alkanesulfonyl-alkyl, alkanesulfonyl-aryl, alkanesulfonyl, arenesulfonyl-alkyl, or arenesulfonyl-aryl, or arenesulfonyl, sulfoamino-alkyl, sulfoamino-aryl, sulfoamino-alkoxy, sulfoamino-aryloxy, sulfoamino, sulfinoamino-alkyl, sulfinoamino-aryl, sulfinoamino-alkoxy, sulfinoamino-aryloxy, sulfinoamino, alkanesulfonylamino-alkyl, alkanesulfonylamino-aryl, alkanesulfonylamino-alkoxy, alkanesulfonylamino-aryloxy, alkanesulfonylamino, arenesulfonylamino-alkyl, arenesulfonylamino-aryl, arenesulfonylamino-alkoxy, arenesulfonylamino-aryloxy, arenesulfonylamino, alkanesulfinylamino-alkyl, alkanesulfinylamino-aryl, alkanesulfinylamino-alkoxy, alkanesulfinylamino-aryloxy, alkanesulfinylamino, arenesulfinylamino-alkyl, arenesulfinylamino-aryl, arenesulfinylamino-alkoxy, arenesulfinylamino-aryloxy, arenesulfinylamino, phosphono-alkyl, phosphono-aryl, phosphono-alkyloxy, phosphono-aryloxy, phosphono, hydroxyphosphinoyl-alkyl, hydroxyphosphinoyl-aryl, hydroxyphosphinoyl-alkyloxy, hydroxyphosphinoyl-aryloxy, hydroxyphosphinoyl, hydroxy-alkyl-phosphinoyl-alkyl, hydroxy-alkyl-phosphinoyl-aryl, hydroxy-alkyl-phosphinoyl-alkyloxy, hydroxy-alkyl-phosphinoyl-aryloxy, hydroxy-alkyl-phosphinoyl, phosphonoamino-alkyl, phosphonoamino-aryl, phosphonoamino-alkoxy, phosphonoamino-aryloxy, phosphonoamino, or, where chemically matching, a salt of the above described substituents.

The present invention further relates to the use of a compound as disclosed in the present invention in the manufacturing of a luminescent compound based on iridium3+. Further, the present invention discloses a method for producing an electrochemiluminescent compound.

DETAILED DESCRIPTION OF THE INVENTION

As indicated above, there is a need for novel bis-iridium-complexes that can be used for manufacturing electrochemiluminescent labels (ECL-labels).

Novel Bis-Iridium-Complexes of Formula I

The present invention relates to an iridium-based chemiluminescent compound of Formula I

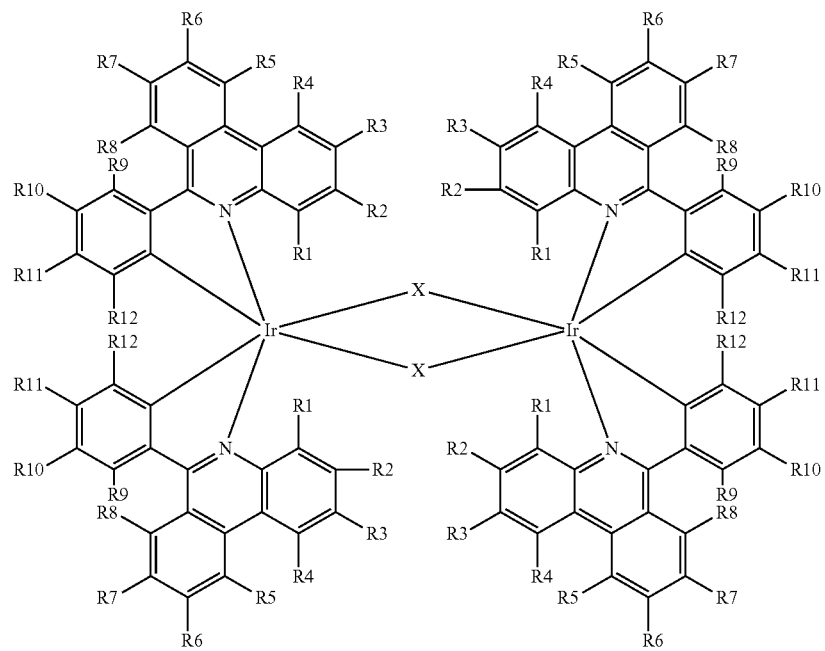

wherein each X is independently chloro, bromo, iodo, hydroxyl, methoxy, ethoxy, phenoxy, cyanato or diphenylphosphanyl, wherein each R1-R12 independently is hydrogen, halide, cyano- or nitro-group, amino, substituted amino, alkylamino, substituted alkylamino, arylamino, substituted arylamino, alkylammonium, substituted alkylammonium, carboxy, carboxylate, carboxylic acid ester, carbamoyl, hydroxy, substituted or unsubstituted alkyloxy, substituted or unsubstituted aryloxy, sulfanyl, substituted or unsubstituted alkylsulfonyl, substituted or unsubstituted arylsulfonyl, sulfo, sulfino, sulfeno, sulfonate, sulfinate, sulfenate, sulfamoyl, sulfoxide, phosphono, hydroxyphosphinoyl, hydroxy-alkyl-phosphinoyl, phosphonate, phosphinate or R13, wherein R13 is aryl, substituted aryl, alkyl, substituted alkyl, branched alkyl, substituted branched alkyl, arylalkyl, substituted arylalkyl, alkylaryl, substituted alkylaryl, alkenyl, substituted alkenyl, alkynyl, substituted alkynyl, amino-alkyl, substituted amino-alkyl, amino-alkoxy, substituted amino-alkoxy, amino-aryl, substituted amino-aryl, amino-aryloxy, substituted amino-aryloxy, wherein within R1-R12 two adjacent Rs can form an aromatic ring or a substituted aromatic ring, wherein the substituent is selected from hydrogen, alkyl, substituted alkyl, halide, cyano- or nitro-group, a hydrophilic group, like amino, substituted amino, alkylamino, substituted alkylamino, alkylammonium, substituted alkylammonium, carboxy, carboxylate, carboxylic acid ester, carbamoyl, hydroxy, substituted or unsubstituted alkyloxy, substituted or unsubstituted aryloxy, sulfanyl, substituted or unsubstituted alkylsulfonyl, substituted or unsubstituted arylsulfonyl, sulfo, sulfino, sulfeno, sulfonate, sulfinate, sulfenate, sulfamoyl, sulfoxide, phosphono, hydroxyphosphinoyl, hydroxyl-alkyl-phosphinoyl, phosphonate, phosphinate or, wherein within R1-R12 two adjacent Rs can form an aliphatic ring or a substituted aliphatic ring, wherein the substituent is selected from hydrogen, alkyl, substituted alkyl, halide, cyano- or nitro-group, a hydrophilic group, like amino, substituted amino, alkylamino, substituted alkylamino, alkylammonium, substituted alkylammonium, carboxy, carboxylate, carboxylic acid ester, carbamoyl, hydroxy, substituted or unsubstituted alkyloxy, substituted or unsubstituted aryloxy, sulfanyl, substituted or unsubstituted alkylsulfonyl, substituted or unsubstituted arylsulfonyl, sulfo, sulfino, sulfeno, sulfonate, sulfinate, sulfenate, sulfamoyl, sulfoxide, phosphono, hydroxyphosphinoyl, hydroxyl-alkyl-phosphinoyl, phosphonate, phosphinate, wherein, if in any of R1-R13 a substitution is present, the substituent in R1-R13 is each independently selected from a halide, cyano- or nitro-group, a hydrophilic group, like an amino, alkylamino, alkylammonium, carboxy, carboxylate, carboxylic acid ester, carbamoyl, hydroxy, alkyloxy, arylalkyloxy, aryloxy, alkylaryloxy, polyethylenoxy, polypropylenoxy, sulfanyl, alkylsulfonyl, arylsulfonyl, sulfo, sulfino, sulfeno, sulfonate, sulfinate, sulfenate, sulfamoyl, sulfoxide, phosphono, hydroxyphosphinoyl, hydroxyl-alkyl-phosphinoyl, phosphonate, phosphinate, wherein alkyl is a linear or branched alkyl chain with a length of 1-20 carbon atoms or a heteroalkyl chain with the length of 1-20 atoms comprising 1-4 heteroatoms selected from O, N, P, and S, and, wherein aryl is a 5, 6, or 7 member aryl ring system, or a 5, 6, or 7 member heteroaryl ring system comprising 1-3 heteroatoms selected from O, S and N, with the proviso that at least one of R1-R12 is a substituted or unsubstituted group selected from sulfo-alkyl, sulfo-aryl, sulfo-alkoxy, sulfo-aryloxy, sulfo, sulfino-alkyl, sulfino-aryl, sulfino-alkoxy, sulfino-aryloxy, sulfino, sulfeno-alkyl, sulfeno-aryl, sulfeno-alkoxy, sulfeno-aryloxy, sulfeno, sulfamoyl-alkyl, sulfamoyl-aryl, sulfamoyl-alkoxy, sulfamoyl-aryloxy, sulfamoyl, alkanesulfonyl-alkyl, alkanesulfonyl-aryl, alkanesulfonyl, arenesulfonyl-alkyl, or arenesulfonyl-aryl, or arenesulfonyl, sulfoamino-alkyl, sulfoamino-aryl, sulfoamino-alkoxy, sulfoamino-aryloxy, sulfoamino, sulfinoamino-alkyl, sulfinoamino-aryl, sulfinoamino-alkoxy, sulfinoamino-aryloxy, sulfinoamino, alkanesulfonylamino-alkyl, alkanesulfonylamino-aryl, alkanesulfonylamino-alkoxy, alkanesulfonylamino-aryloxy, alkanesulfonylamino, arenesulfonylamino-alkyl, arenesulfonylamino-aryl, arenesulfonylamino-alkoxy, arenesulfonylamino-aryloxy, arenesulfonylamino, alkanesulfinylamino-alkyl, alkanesulfinylamino-aryl, alkanesulfinylamino-alkoxy, alkanesulfinylamino-aryloxy, alkanesulfinylamino, arenesulfinylamino-alkyl, arenesulfinylamino-aryl, arenesulfinylamino-alkoxy, arenesulfinylamino-aryloxy, arenesulfinylamino, phosphono-alkyl, phosphono-aryl, phosphono-alkyloxy, phosphono-aryloxy, phosphono, hydroxyphosphinoyl-alkyl, hydroxyphosphinoyl-aryl, hydroxyphosphinoyl-alkyloxy, hydroxyphosphinoyl-aryloxy, hydroxyphosphinoyl, hydroxy-alkyl-phosphinoyl-alkyl, hydroxy-alkyl-phosphinoyl-aryl, hydroxy-alkyl-phosphinoyl-alkyloxy, hydroxy-alkyl-phosphinoyl-aryloxy, hydroxy-alkyl-phosphinoyl, phosphonoamino-alkyl, phosphonoamino-aryl, phosphonoamino-alkoxy, phosphonoamino-aryloxy, phosphonoamino, or, where chemically matching, a salt of the above described substituents.

The compound according to Formula I is referred to herein as bis-iridium complex or as iridium dimer (complex). It is a dinuclear (iridium) complex and it is also named a di-iridium complex.

As defined above each the two "bridging groups" X in Formula I independently is chloro, bromo, iodo, hydroxyl, methoxy, ethoxy, phenoxy, cyanato or diphenylphosphanyl.

In one embodiment each of the two "bridging groups" X in Formula I independently is selected from the group consisting of chloro, bromo, iodo, hydroxyl, methoxy, and cyanato.

In one embodiment each of the two "bridging groups" X in Formula I independently is selected from the group consisting of chloro, bromo and iodo.

In one embodiment each of the two "bridging groups" X in Formula I is chloro.

As the skilled person will appreciate, in certain embodiments the two "bridging groups" X in Formula I will be the same and as defined above.

In one embodiment, if in any of R1-R13 a substitution is present, the substituent in R1-R13 is each independently selected from a halide, cyano- or nitro-group, a hydrophilic group, like an amino, alkylamino, alkylammonium, carboxy, carboxylate, carboxylic acid ester, carbamoyl, hydroxy, alkyloxy, arylalkyloxy, aryloxy, alkylaryloxy, polyethylenoxy, polypropylenoxy, sulfanyl, alkylsulfonyl, arylsulfonyl, sulfo, sulfonate, and phosphono. In one embodiment, if in any of R1-R13 a substitution is present, the substituent in R1-R13 is each independently selected from a halide, amino, carboxy, carboxylate, carboxylic acid ester, hydroxy, alkyloxy, polyethylenoxy, alkylsulfonyl, sulfo and sulfonate.

In one embodiment, if in any of R1-R13 a substitution is present, the substituent in R1-R13 is each independently selected from amino, carboxy, hydroxy, and sulfo and sulfonate.

In one embodiment, in none of R1-R13 a substitution is present.

As used herein, including the accompanying claims, the substituents have the meanings commonly known to the skilled person.

Alkyl, preferably, is a linear or branched alkyl chain with a length of 1-20 carbon atoms, preferably with a length of 1-10 carbon atom, particular preferred with a length of 1-6 carbon atoms; or a heteroalkyl chain with the length of 1-20 atoms, preferably with a length of 1-10 carbon atom, comprising 1-4 heteroatoms selected from O, N, P, and S. Examples of alkyl groups include, but are not limited to, methyl, ethyl, propyl, isopropyl, butyl, isobutyl, tert.-butyl, the isomeric pentyls, the isomeric hexyls, the isomeric heptyls, the isomeric octyls, and dodecyl. In a particular preferred embodiment, alkyl is methyl or ethyl.

The terms alkoxy and alkyloxy as well as substituted alkyl and substituted alkoxy, respectively, may be used interchangeably. Alkoxy and alkyloxy mean a moiety of the formula —OR, wherein R preferably is an alkyl moiety as defined hereinabove. Examples of alkoxy moieties include, but are not limited to, methoxy, ethoxy, and isopropoxy.

Aryl, preferably, is a 5, 6, or 7 member aryl ring system, preferably a 6 member aryl ring system, or a 5, 6, or 7 member heteroaryl ring system comprising 1-3 heteroatoms selected from 0, S and N, preferably a 6 member heteroaryl ring system. In a particular preferred embodiment, aryl is phenyl.

In one embodiment, in Formula I each R1-R12 independently is hydrogen, hydroxy, substituted or unsubstituted alkyloxy, substituted or unsubstituted aryloxy, sulfanyl, substituted or unsubstituted alkylsulfonyl, substituted or unsubstituted arylsulfonyl, sulfo, sulfino, sulfeno, sulfonate, sulfinate, sulfenate, sulfamoyl or sulfoxide.

In one embodiment, in Formula I each R1-R12 independently is hydrogen, substituted or unsubstituted alkyloxy, substituted or unsubstituted aryloxy, substituted or unsubstituted alkylsulfonyl, substituted or unsubstituted arylsulfonyl, sulfonate, sulfinate, sulfenate, sulfamoyl or sulfoxide.

In one embodiment, in Formula I each R1-R12 independently is hydrogen, substituted or unsubstituted alkyloxy, substituted or unsubstituted alkylsulfonyl, substituted or unsubstituted arylsulfonyl, sulfonate or sulfoxide.

In one embodiment, in Formula I each R1-R12 independently is hydrogen, unsubstituted alkyloxy, unsubstituted alkylsulfonyl, unsubstituted arylsulfonyl, sulfonate or sulfoxide.

In one embodiment at least one of R1 to R12 is a substituted or unsubstituted group selected from sulfo-alkyl, sulfo-aryl, sulfo-alkoxy, sulfo-aryloxy, sulfo, sulfamoyl-alkyl, sulfamoyl-aryl, sulfamoyl-alkoxy, sulfamoyl-aryloxy, sulfamoyl, alkanesulfonyl-alkyl, alkanesulfonyl-aryl, alkanesulfonyl, arenesulfonyl-alkyl, arenesulfonyl-aryl, arenesulfonyl, alkanesulfonylamino-alkyl, alkanesulfonylamino-aryl, alkanesulfonylamino-alkoxy, alkanesulfonylamino-aryloxy, alkanesulfonylamino, arenesulfonylamino-alkyl, arenesulfonylamino-aryl, arenesulfonylamino-alkoxy, arenesulfonylamino-aryloxy, arenesulfonylamino, phosphono-alkyl, phosphono-aryl, phosphono-alkyloxy, phosphono-aryloxy, phosphono, hydroxyphosphinoyl-alkyl, hydroxyphosphinoyl-aryl, hydroxyphosphinoyl-alkyloxy, hydroxyphosphinoyl-aryloxy, hydroxyphosphinoyl, hydroxy-alkyl-phosphinoyl-alkyl, hydroxy-alkyl-phosphinoyl-aryl, hydroxy-alkyl-phosphinoyl-alkyloxy, hydroxy-alkyl-phosphinoyl-aryloxy, hydroxy-alkyl-phosphinoyl, or, where chemically matching, a salt of the above described substituents.

In one embodiment at least one of R1 to R12 is a substituted or unsubstituted group selected from sulfo-alkyl, sulfo-aryl, sulfo-alkoxy, sulfo-aryloxy, sulfo, or a salt thereof (=sulfonate), wherein the counter ion preferably is a cation from the group of alkali metals.

In one embodiment at least one of R1 to R12 is sulfo-alkyl, sulfo-aryl, sulfo-alkoxy, sulfo-aryloxy, sulfo, or a salt thereof (=sulfonate), wherein the counter ion preferably is a cation from the group of alkali metals.

In one embodiment at least one of R1 to R12 is a substituted or unsubstituted group selected from sulfo-alkyl, sulfo-alkoxy, sulfo, or a salt thereof (=sulfonate), wherein the counter ion is a cation from the group of alkali metals.

In one embodiment at least one of R1 to R12 is sulfo-alkyl, sulfo-alkoxy, sulfo, or a salt thereof (=sulfonate), wherein the counter ion is a cation from the group of alkali metals.

In one embodiment at least one of R1 to R12 is sulfo-methyl, sulfo-alkoxy with a C2 to C4 alkyl chain, or a salt thereof (=sulfonate) wherein the counter ion is a cation from the group of alkali metals.

In one embodiment at least one of the groups R1 to R12 of Formula I is a sulfo group.

In one embodiment, the counter ion is an alkali metal cation selected from the group consisting of lithium cation, sodium cation, potassium cation and caesium cation.

In one embodiment, the counter ion is an alkali metal cation selected from the group consisting of sodium cation and caesium cation.

In one embodiment, the counter ion is a caesium cation.

In one embodiment, in Formula I each of the two "bridging groups" X independently is selected from the group consisting of chloro, bromo, iodo, hydroxyl, methoxy, and cyanato, each R1-R12 independently is hydrogen, hydroxy, substituted or unsubstituted alkyloxy, substituted or unsubstituted aryloxy, sulfanyl, substituted or unsubstituted alkylsulfonyl, substituted or unsubstituted arylsulfonyl, sulfo, sulfino, sulfeno, sulfonate, sulfinate, sulfenate, sulfamoyl or sulfoxide, if in any of R1-R12 a substitution is present, the substituent in R1-R13 is each independently selected from a halide, cyano- or nitro-group, a hydrophilic group, like an amino, alkylamino, alkylammonium, carboxy, carboxylate, carboxylic acid ester, carbamoyl, hydroxy, alkyloxy, arylalkyloxy, aryloxy, alkylaryloxy, polyethylenoxy, polypropylenoxy, sulfanyl, alkylsulfonyl, arylsulfonyl, sulfo, sulfonate, and phosphono, and at least one of R1 to R12 is a substituted or unsubstituted group selected from sulfo-alkyl, sulfo-aryl, sulfo-alkoxy, sulfo-aryloxy, sulfo, or a salt thereof (=sulfonate), wherein the counter ion preferably is a cation from the group of alkali metals.

In one embodiment the phenyl-phenanthridine residues comprised in Formula I are selected from the below given substituted phenyl-phenanthridines.

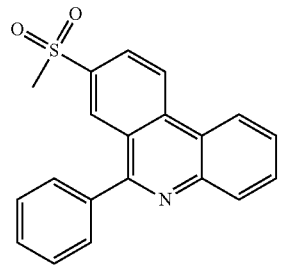

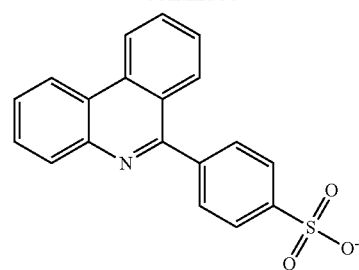
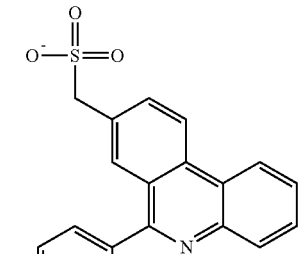
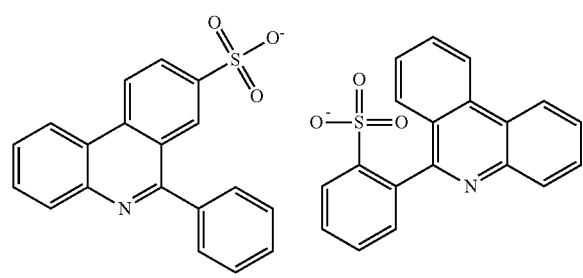
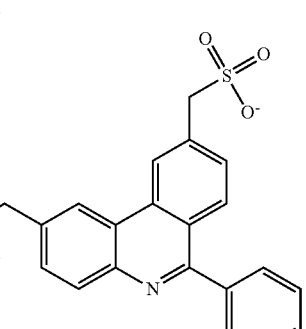
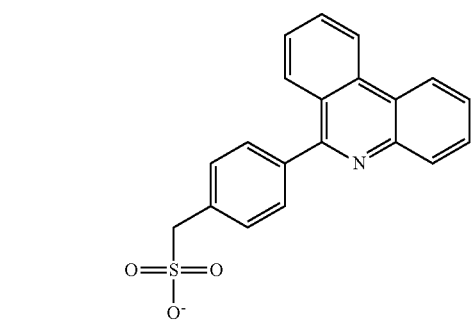
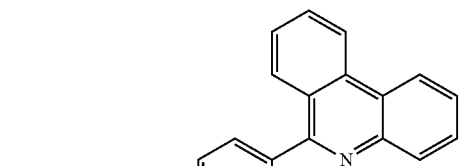
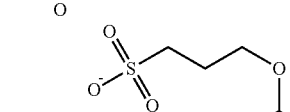
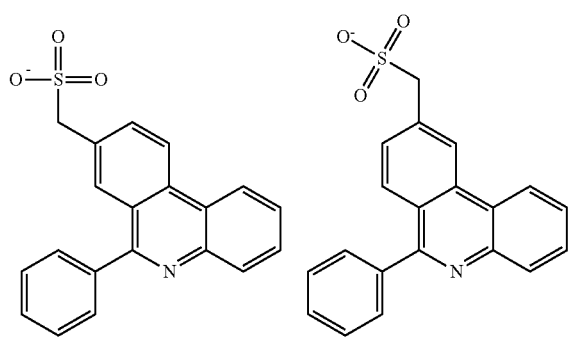
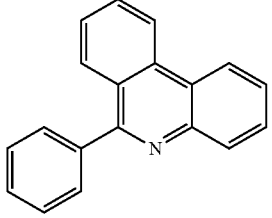
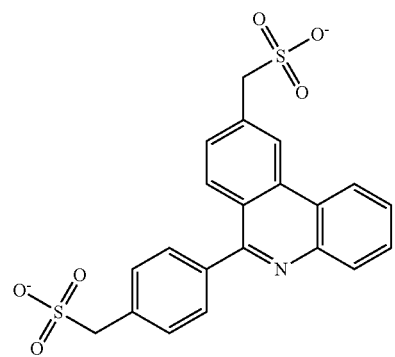
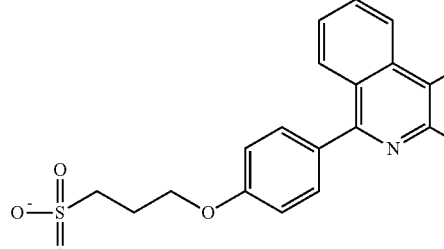

In one embodiment, the phenyl-phenanthridine residues comprised in Formula I are selected from the substituted phenyl-phenanthridines depicted above and X is chloro.

Any combinations of any embodiments of the compounds of Formula I as defined above are considered to be within the scope of the invention.

Process for the Preparation of the Novel Bis-Iridium-Complexes of Formula I

The invention, in another aspect, relates to a novel process for the preparation of compounds of Formula I.

Compounds according to Formula I can e.g. be synthesized (based on Nonoyama, M., J. Organomet. Chem. 86 (1975) 263-267) as follows and as e.g. shown in Example 3.

Thus, in one aspect, the invention relates to a process for the preparation of a compound of Formula I as defined above, comprising the following step:

Reaction of a phenyl-phenanthridine residue as defined above via the compound of Formula I with a iridium trihalogenide, preferably with iridium trichloride trihydrate, if appropriate in the presence of a solvent, to obtain a compound of Formula I as defined above.

If the process is carried out in the presence of a solvent, suitable solvents for carrying out the process of the invention may include organic solvents. These preferably include 2-ethoxyethanol or methoxyethanol, and mixtures thereof with water; a 2-ethoxyethanol/water mixture is preferred.

In one embodiment, the process is carried out in a 2-ethoxyethanol/water mixture.

In one embodiment, the process is carried out in the presence of an inorganic or organic base. This preferably include a trialkylamine base.

In one embodiment, the process is carried out under inert gas atmosphere, preferably under nitrogen.

In accordance with this process a compound of Formula I can be e.g. obtained as shown in Scheme 1 below.)

Scheme 1: Synthesis of a compound of Formula I.

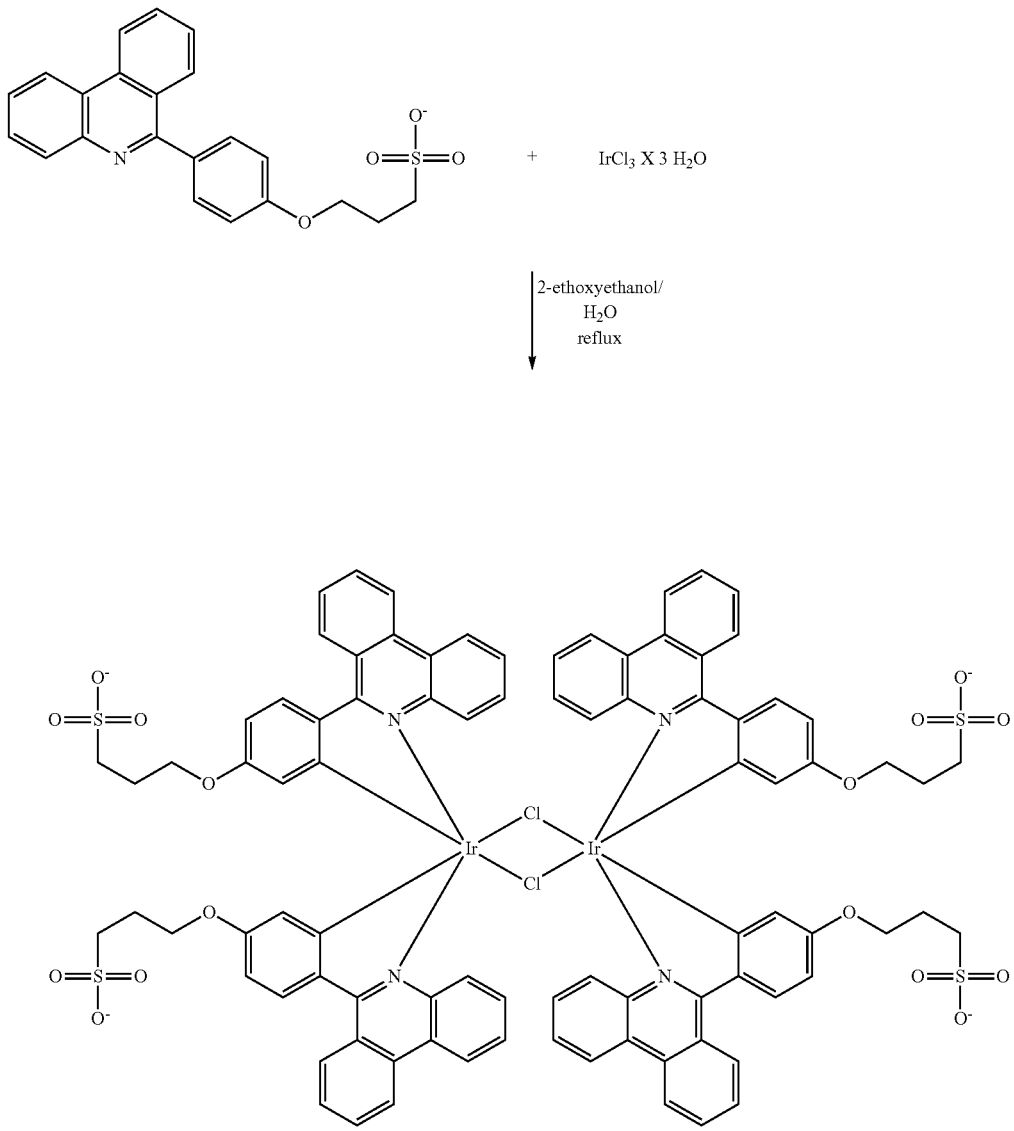

The phenyl-phenanthridines, e.g. sulfonate substituted phenyl-phenanthridines, used as starting material can be obtained by processes as e.g. shown in the Examples (cf. Examples 3.1 and 3.3). The compound (4-phenanthridin-6-yl-phenyl)-methanesulfonic acid isobutyl ester is novel and also subject-matter of the present invention Use of the Bis-Iridium-Complexes of the Invention for Manufacturing Electrochemiluminescent Labels (ECL-Labels)

In one aspect, the compound according to Formula I, i.e. the iridium dimer complex comprising four times a phenyl-phenanthridine derivative and two iridium 3+ atoms, is used in the manufacturing of a luminescent label. As the skilled person will appreciate such a label is a monomer or monomeric Ir3+ complex and comprises twice a phenyl-phenanthridine derivative as defined via Formula I and a third ligand. Preferably the resulting luminescent label is an electrochemiluminescent label.

The third ligand strongly influences the light emission properties of the resulting iridium-label.

In one embodiment the present invention relates to the use of a bis-iridium complex according to Formula I in the manufacturing of a luminescent label, wherein the third ligand is selected from the group consisting of a derivative of picolinic acid, a derivative of azolyl pyridine, a derivative of bipyridyl, a derivative of phenyl-pyridine, and a derivative of phenylazole.

In one embodiment the present invention relates to the use of a bis-iridium complex according to Formula I in the manufacturing of a luminescent label comprising twice a phenyl-phenanthridine derivative as defined via Formula I and a derivative of picolinic acid as the third ligand, as described e.g. in EP 12179048.9.

A "derivative of picolinic acid" is defined by Formula II

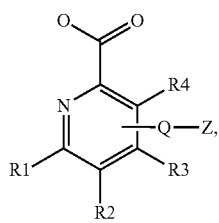

FORMULA II wherein R1 to R4 are as defined above for R1 to R12 of Formula I with the proviso that at least one of R1 to R4 is -Q-Z, wherein Q is a linker or a covalent bond, and wherein Z is a functional group.

Preferred embodiments of R1 to R4 are as defined above for R1 to R12 of Formula I.

Preferred embodiments of Q and Z, respectively, are defined below.

In one embodiment, one of R1 to R4 is -Q-Z, wherein Q is a linker or a covalent bond, and wherein Z is a functional group, and the other groups R1 to R4 are hydrogen.

In one embodiment the present invention relates to the use of a bis-iridium complex according to Formula I in the manufacturing of a luminescent label comprising twice a phenyl-phenanthridine derivative as defined via Formula I and a derivative of azolyl pyridine as the third ligand, as e.g. described in EP 12179050.5.

A "derivative of azolyl pyridine" is defined by Formula III

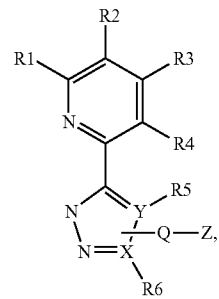

FORMULA III wherein X represents C or N,
wherein Y represents C or N,
wherein R1 to R6 are as defined above for R1 to R12 of Formula I with the proviso that at least one of R1 to R6 is -Q-Z,
wherein Q is a linker or a covalent bond, and
wherein Z is a functional group.

Preferred embodiments of R1 to R6 are as defined above for R1 to R12 of Formula I.

Preferred embodiments of Q and Z, respectively, are defined below.

In one embodiment, one of R1 to R6 is -Q-Z, wherein Q is a linker or a covalent bond, and wherein Z is a functional group, and the other groups R1 to R6 are hydrogen.

In one embodiment the present invention relates to the use of a bis-iridium complex according to Formula I in the manufacturing of a luminescent label comprising twice a phenyl-phenanthridine derivative as defined via Formula I and a derivative of bipyridyl as the third ligand, as e.g. described in EP 12179054.7.

A "derivative of bipyridyl" is defined in Formula IV

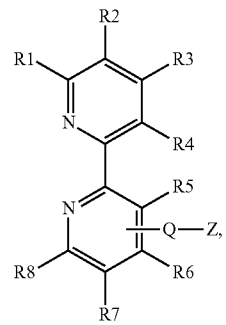

FORMULA IV wherein R1 to R8 are as defined above for R1 to R12 of Formula I with the proviso that at least one of R1 to R8 is -Q-Z,
wherein Q is a linker or a covalent bond, and
wherein Z is a functional group.

Preferred embodiments of R1 to R8 are as defined above for R1 to R12 of Formula I.

Preferred embodiments of Q and Z, respectively, are defined below.

In one embodiment, one of R1 to R8 is -Q-Z, wherein Q is a linker or a covalent bond, and wherein Z is a functional group, and the other groups R1 to R8 are hydrogen.

In one embodiment the present invention relates to the use of a bis-iridium complex according to Formula I in the manufacturing of a luminescent label comprising twice a phenyl-phenanthridine derivative as defined via Formula I and a derivative of phenyl-pyridine as the third ligand, as e.g. described in EP 12179054.7.

A "derivative of phenyl-pyridine" is defined in Formula V

FORMULA V

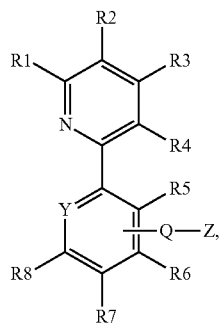

wherein in one of X and Y is N and the other is C, wherein R1 to R8 are as defined above for R1 to R12 of Formula I with the proviso that at least one of R1 to R8 is -Q-Z, wherein Q is a linker or a covalent bond, and wherein Z is a functional group.

Preferred embodiments of R1 to R8 are as defined above for R1 to R12 of Formula I.

Preferred embodiments of Q and Z, respectively, are defined below.

In one embodiment, one of R1 to R8 is -Q-Z, wherein Q is a linker or a covalent bond, and wherein Z is a functional group, and the other groups R1 to R8 are hydrogen.

In one embodiment the present invention relates to the use of a bis-iridium complex according to Formula I in the manufacturing of a luminescent label comprising twice a phenyl-phenanthridine derivative as defined via Formula I and a derivative of phenylazolyle as the third ligand, as e.g. described in EP 12179057.0.

A "derivative of phenylazole" is defined in Formulae VIa and VIb

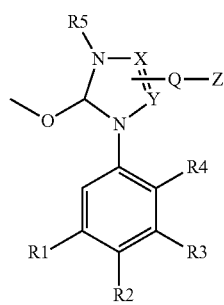

VIa

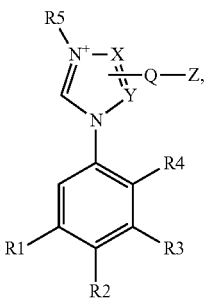

VIb wherein X and Y are C—R6 and C—R7, respectively, or wherein one of X and Y is N and the other is C—R7 or C—R6, respectively, wherein R1 to R7 are as defined above for R1 to R12 of Formula I with the proviso that at least one of R1 to R7 is -Q-Z, wherein Q is a linker or a covalent bond, and wherein Z is a functional group.

Preferred embodiments of R1 to R7 are as defined above for R1 to R12 of Formula I.

Preferred embodiments of Q and Z, respectively, are defined below.

In one embodiment, one of R1 to R7 is -Q-Z, wherein Q is a linker or a covalent bond, and wherein Z is a functional group, and the other groups R1 to R7 are hydrogen.

In one embodiment the present invention relates to the use of a bis-iridium complex according to Formula I in the manufacturing of a luminescent label, wherein the third ligand is selected from the group consisting of a derivative of picolinic acid, a derivative of azolyl pyridine, a derivative of bipyridyl, and a derivative of phenyl-pyridine.

In the compounds according Formulas II, III, IV, V and VI, respectively, Q either is a covalent bond or a linker having a backbone length of between 1 and 200 atoms. With other words if the backbone length is between 1 and 200 atoms, the shortest connection between the aromatic ring of a ligand according to any of Formulas II, III, IV, V, and VI, respectively, and the functional group Z consists of 1 to 200 atoms.

In case a ring system is present the shortest number of atoms in the ring system is taken when assessing the linker length. As an example, a phenylene ring accounts for a length of four atoms in a linker.

In one embodiment Q is a covalent bond or a linker having as a backbone a straight or branched saturated, unsaturated, unsubstituted or substituted C1-C200 alkyl chain, or a 1 to 200 atom chain consisting of carbon atoms, substituted carbon atoms and/or one or more atoms selected from O, N, P and S, or substituted N, P, S atoms, or a chain as described before with the backbone containing one or more cyclic or heterocyclic aromatic or non-aromatic ring systems.

In one embodiment the linker Q has as a backbone a straight or branched saturated, unsaturated, unsubstituted or substituted C1-C100 alkyl chain, or a 1 to 100 atom chain consisting of carbon atoms, substituted carbon atoms and/or one or more atoms selected from O, N, P and S, or substituted N, P, or S atoms, or a chain as described before with the backbone containing one or more cyclic or heterocyclic aromatic or non-aromatic ring systems.

In one embodiment the linker Q has as a backbone a straight or branched saturated, unsaturated, unsubstituted or substituted C1-C50 alkyl chain, or a 1 to 50 atom chain consisting of carbon atoms, substituted carbon atoms and/or one or more atoms selected from O, N, P and S, or substituted N, P, or S atoms, or a chain as described before with the backbone containing one or more cyclic or heterocyclic aromatic or non-aromatic ring systems.

In one further embodiment the linker Q has as a backbone a straight or branched saturated, unsaturated, unsubstituted or substituted C1-C20 alkyl chain, or a 1 to 20 atom chain consisting of carbon atoms, substituted carbon atoms and/or one or more atoms selected from O, N, P and S, or substituted N, P, or S atoms, or a chain as described before with the backbone containing one or more cyclic or heterocyclic aromatic or non-aromatic ring systems.

In one embodiment, the linker Q in the electrochemiluminescent complex of this invention is a straight or branched saturated, unsaturated, unsubstituted, substituted C1-C20 alkyl chain, or a C1-C20 arylalkyl chain (wherein e.g. a phenylene ring accounts for a length of four carbon atoms), or a 1 to 20 atom chain with a backbone consisting of carbon atoms, substituted carbon atoms and/or one or more atoms selected from O, N, P and S, or substituted N, P, or S atoms, or a 1 to 20 atom chain, or with a backbone consisting of carbon atoms, substituted carbon atoms and one or more atoms selected from O, N, P and S, or substituted N, P, or S atoms comprising at least one aryl, heteroaryl, substituted aryl or substituted heteroaryl group (wherein e.g. a phenylene ring accounts for a length of four atoms).

In one embodiment the linker Q in a compound according to the present invention is a saturated C1-C12 alkyl chain, or a C1-C12 arylalkyl chain, or a 1 to 12 atom chain with a backbone consisting of carbon atoms, substituted carbon atoms and one or more atoms selected from O, N, P and S, or substituted N, P, or S atoms, or a 1 to 12 atom chain with a backbone consisting of carbon atoms, substituted carbon atoms and one or more atoms selected from O, N, P and S, or substituted N, P, or S atoms comprising at least one aryl, heteroaryl, substituted aryl or substituted heteroaryl group (wherein e.g. a phenylene ring accounts for a length of four atoms).

The term "linker" as used herein, has the meaning known to a person skilled in the art and relates to a molecule or groups of molecules, which are used to link fragments of molecules. Linkers are characterized by having two or more chemically orthogonal functionalities on a flexible or rigid scaffold.

In one embodiment one of R1 to R4 of Formula II, or one of R1 to R6 of Formula III, or one of R1 to R8 of Formula IV, or one of R1 to R8 of Formula V, or one of R1 to R7 of Formula VI, respectively is -Q-Z.

In one embodiment the functional group Z comprised in the third ligand according to Formulas II, III, IV, V, or VI, respectively, is selected from the group consisting of aldehyde, carboxylic acid, carboxylic acid ester, N-hydroxysuccinimide ester, epoxide, amino group, halogen, hydrazine, hydroxyl, sulfhydryl, maleimido, alkynyl, azide and phosphoramidite.

In one embodiment the functional group Z comprised in the third ligand according to Formulas II, III, IV, V, or VI, respectively, is selected from the group consisting of carboxylic acid, amino group, halogen, sulfhydryl, maleimido, alkynyl and azide.

Methods for Producing Electrochemiluminescent Compounds and Labels

Further the present invention discloses a method for producing an electrochemiluminescent compound the method comprising the reaction of a dimer as described above with a third ligand, e.g. with a third ligand as described above, in an organic solvent in the presence or absence of a base under inert gas atmosphere.

In one embodiment the reaction of a dimer as described above with a third ligand, e.g. with a third ligand as described above, is performed in dimethylformamide (DMF) in the presence of a base under inert gas atmosphere.

In one embodiment the base used is a carbonate salt of an alkalimetal.

In one embodiment the base used is caesium carbonate.

As mentioned, the compounds as disclosed herein have quite favorable properties. For example the disclosed compounds, i.e., the iridium-based labels manufactured using these compounds, show a high ECL efficiency. This high efficiency is also present if the corresponding measurements are performed in an aqueous system as compared to many, many ECL-labels that only have shown high ECL-efficiency when analyzed in an organic solvent. E.g., many OLED dyes usually are analyzed in acetonitrile and either are not soluble in an aqueous solution or, if soluble, do not show efficient electrochemiluminescence in an aqueous solution.

In one aspect, the present invention relates to the use of a compound of Formula I of the invention as a starting material in the manufacturing of an electrochemiluminescent label.

In one preferred embodiment the present invention relates to the use of a compound as disclosed in the present invention for manufacturing of a label showing an electrochemiluminescense reaction in an aqueous solution. An aqueous solution is any solution comprising at least 90% water (weight by weight). Obviously such aqueous solution may contain in addition ingredients like buffer compounds, detergents and for example tertiary amines like tripropylamine as electron donor in the ECL reaction.

The following examples are provided to aid the understanding of the present invention, the true scope of which is set forth in the appended claims. It is understood that modifications can be made in the procedures set forth without departing from the spirit of the invention.

All publications identified herein are incorporated herein by reference in their entirety.

EXAMPLES

Example 1

Synthesis of Substituted Phenyl-Phenanthridines

Example 1.1

General Procedure for the Synthesis of Substituted 2-Aminobiphenyls

With the Suzuki-Miyaura coupling reaction as described by Youn, S. W., in Tetrahedron Lett. 50 (2009) 4598-4601, between commercially available 2-bromoaniline derivates and the corresponding arylboronic acid the appropriate 2-aminobiphenyls can be synthesized, which are required for further reactions to phenanthridines.

Typical Procedure:

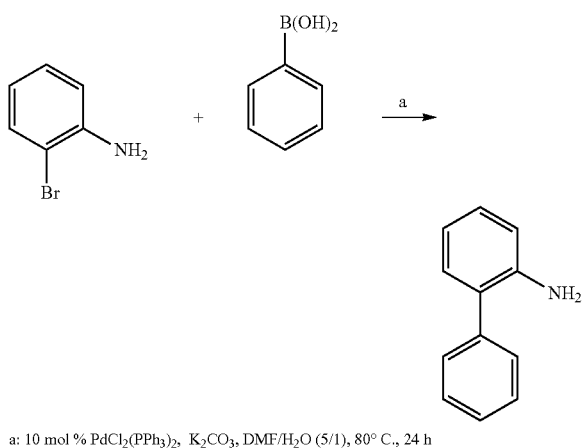

a: 10 mol % PdCl$_2$(PPh$_3$)$_2$, K$_2$CO$_3$, DMF/H$_2$O (5/1), 80° C., 24 h temperature. The resulting mixture was refluxed with stirling for the next 2 hours. The reaction mixture was treated by the dropwise addition of pyridine (0.02 mol in 10 ml chloroform) over a period of 60 minutes. The mixture was allowed to cool to room temperature and stirred overnight. The mixture was washed well with 0.5 M HCl, dried over MgSO$_4$ and concentrated in vacuum. The crude product was purified by flash chromatography on silica gel, 3:2 hexane/ethyl acetate to give pure product 3 in 66% yield.

Benzamido-2-biphenyl 3 (0.01 mol) and POCl$_3$ (5 ml) in 20 ml of toluene were refluxed and stirred under nitrogen for 18 hours, following the procedure described by Lion, C., in Bull. Soc. Chim. Belg. 98 (1989) 557-566. The cooled reaction mixture was diluted with CH$_2$Cl$_2$ (30 ml) and poured into ice, washed with 25% NH$_4$OH and distilled water. The organic layer was dried over MgSO$_4$ and concentrated in vacuo, followed by flash chromatography (silica gel, 1:1 hexane/ethyl acetate) gave the product 4, 6-phenyl-phenanthridine.

Other Examples

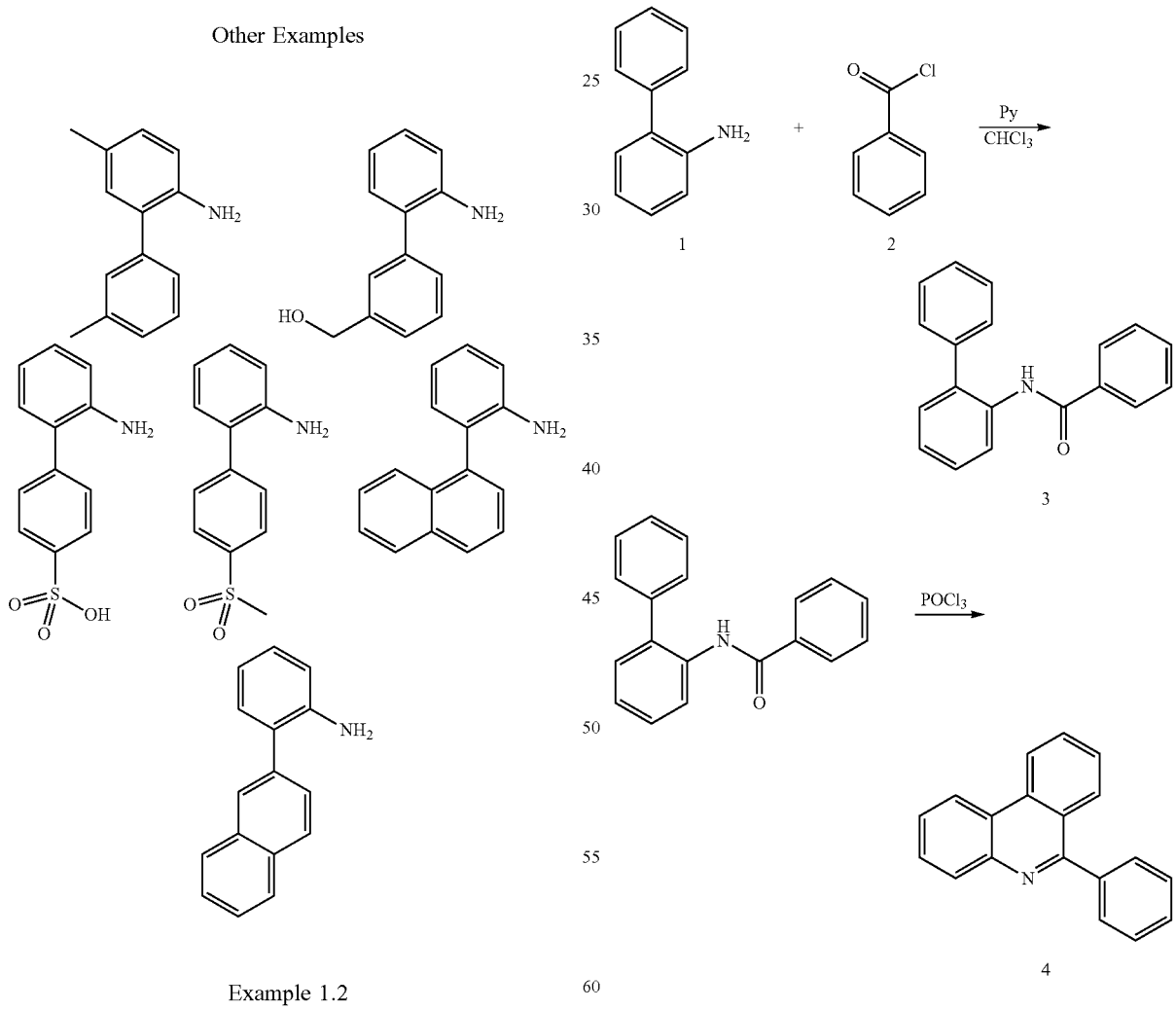

Example 1.2

General Procedure for the Synthesis of Substituted Phenanthridines

To the ice-cooled solution of 2-arylaniline 1 (0.01 mol) in chloroform (20 ml) was added aryl acid chloride 2 (0.01 mol) and stirred under inert condition for 30 min at room Yield:

52%. White solid. $^1$H NMR (CDCl$_3$, 400 MHz) δ 7.54-7.85 (m, 9H), 8.10 (d, J=8.0 Hz, 1H), 8.28 (d, J=7.9 Hz, 1H), 8.62 (d, J=8.4 Hz, 1H), 8.67 (d, J=8.4 Hz, 1H).

Using 2-naphthalen-2-yl-phenylamine instead of 2-arylaniline yields:

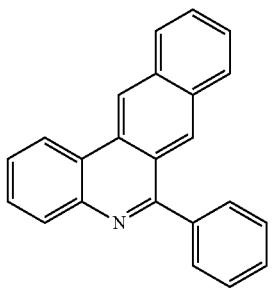 [SMILES: c1ccc(-c2nc3ccccc3c3cc4ccccc4cc23)cc1]

¹H-NMR (400 MHz, CDCl₃) δ 8.64 (d, J=9.1 Hz, 2H), 8.29 (d, J=8.1 Hz, 1H), 8.16 (d, J=8.92 Hz, 1H), 7.92 (d, J=7.48 Hz, 1H), 7.79-7.75 (m, 2H), 7.69 (t, J=14.0, 8.2 Hz, 1H), 7.63-7.61 (m, 2H), 7.53-7.46 (m, 4H), 7.19 (t, J=14.3, 7.2 Hz, 1H).

MS:
[M+H]⁺ 306.3

Using naphthalene-carbonyl chloride instead of phenyl acid chloride yields:

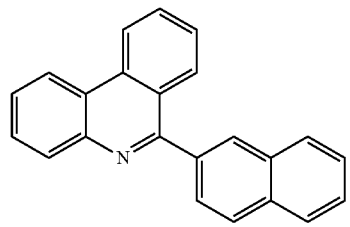 [SMILES: c1ccc2cc(-c3nc4ccccc4c4ccccc34)ccc2c1]

¹H-NMR (400 MHz, CDCl₃) δ 8.74 (d, J=8.3 Hz, 1H), 8.65 (d, J=8.1 Hz, 1H), 8.27 (d, J=8.1 Hz, 1H), 8.23 (s, 1H), 8.15 (d, J=8.3 Hz, 1H), 8.03 (d, J=8.4 Hz, 1H), 7.97-7.94 (m, 2H), 7.90-7.85 (m, 2H), 7.80-7.69 (m, 2H), 7.62 (t, J=14.2, 7.1 Hz, 1H), 7.59-7.55 (m, 2H).

MS:
[M+H]⁺ 306.3

Example 1.3

Procedure for the Synthesis of 6-(2-sulfophenyl) Phenanthridine

The 6-(2-sulfophenyl)phenanthridine can be synthesized by gentle heating of arylaniline (0.01 mol) with 2-sulfobenzoic acid cyclic anhydride (0.01 mol) in CH₃CN for 6 hours using the procedure as described by Nicolai, E., in Chem. Pharm. Bull. 42 (1994) 1617-1630.

After purification the product can be converted to the appropriate phenanthridine based on the method described in example 1.2.

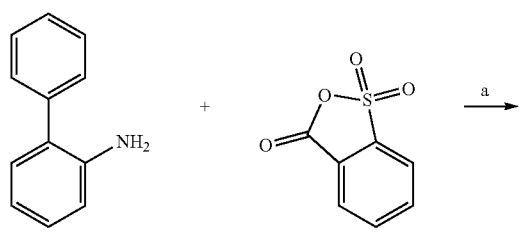

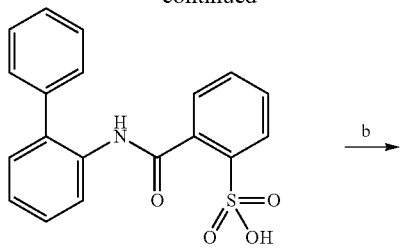

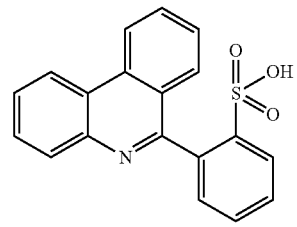

Example 1.4

Procedure for the Synthesis of 6-phenyl-alkylsulfonyl Phenanthridine

The 6-phenyl-alkylsulfonyl phenanthridine can be synthesized by gentle heating of alkylsulfonyl-arylaniline (0.01 mol) with benzoic acid chloride (0.01 mol) in chloroform using the procedure as described by Lion, C., in Bull. Soc. Chim. Belg. 98 (1989) 557-566, see example 1.2.

After purification the product can be converted to the appropriate phenanthridine based on the method described in example 1.2.

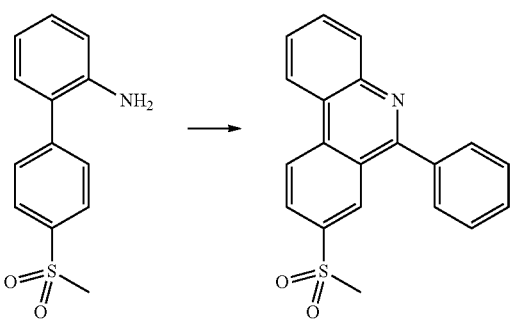 [SMILES: CS(=O)(=O)c1ccc(-c2ccccc2N)cc1 ; CS(=O)(=O)c1ccc2c(c1)c(-c1ccccc1)nc1ccccc12]

¹H-NMR (400 MHz, CDCl₃) δ 8.92 (d, J=8.7 Hz, 1H), 8.75 (d, J=1.9 Hz, 1H), 8.68 (d, J=7.0 Hz, 1H), 8.35 (dd, J=8.7, 2.0 Hz, 1H), 8.30 (d, J=7.2 Hz, 1H), 7.89 (t, J=15.3, 7.1 Hz, 1H), 7.81-7.73 (m, 3H), 7.64-7.56 (m, 3H) 3.12 (s, 3H).

MS: [M+H]+ 334.3

The 6-(4-methylsulfophenyl)phenanthridine can be also prepared by following the procedure described by Cymerman, J., in J. Chem. Soc. (1949) 703-707.

Example 1.5

Synthesis of 6-[4-(2-{2-[2-(2-methoxy-ethoxy)-ethoxy]-ethoxy}-ethoxy)-phenyl]-phenanthridine

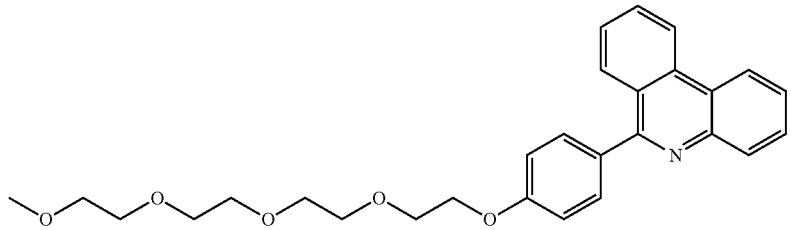 [SMILES: COCCOCCOCCOCCOc1ccc(-c2nc3ccccc3c3ccccc23)cc1]

Synthesis of 2,5,8,11-tetraoxatridecan-13-ol Tosylate

Procedure:

(JACS, 2007, 129, 13364) To a solution of 2,5,8,11-tetraoxatridecan-13-ol (7 g, 33.6 mmol) and triethylamine (4.9 ml, 35.3 mmol) in dry $CH_2Cl_2$ (100 ml), 4-toluenesulfonyl chloride (6.7 g, 35.3 mmol) and DMAP (120 mg) were added.

The mixture was stirred at room temperature for 20 h. The reaction mixture was washed with 80 mL of HCl (1M) and then water. The extract was dried over anhydrous $MgSO_4$, filtrated, and the filtrate was evaporated. The residue was used in the next step without further purification.

Yield:

11.0 g (90%)

NMR:

$^1$H NMR (400 MHz, $CDCl_3$) δ 7.75-7.64 (m, 2H), 7.31-7.26 (m, 2H), 4.16-4.06 (m, 2H), 3.62 (m 2H), 3.59-3.40 (m, 10H), 3.30 (s, 3H), 2.38 (s, 3H).

$^{13}$C{$^1$H} NMR (101 MHz, $CDCl_3$) δ 144.75 (s), 132.90 (s), 129.77 (s), 127.8 (s), 71.82 (s), 70.60 (s), 70.48 (s), 70.47 (s), 70.41 (s), 70.39 (s), 69.23 (s), 68.55 (s), 58.90 (s), 21.53 (s).

Synthesis of 4-PEG4-benzoic Acid Ethyl Ester

Procedure:

(JACS, 2007, 129, 13364) A mixture of compound ethyl 2,5,8,11-tetraoxatridecan-13-yl 4-methylbenzenesulfonate (8.1 g, 22.3 mmol), 4-hydroxybenzoic acid ethyl ester (3.7 g, 22.3 mmol), $K_2CO_3$ (15.4 g, 111.5 mmol) and 18-crown-6 (0.59 g, 2.2 mmol) was refluxed in acetone (120 ml) for 22 h. The reaction mixture was concentrated and extracted with ethyl acetate. The extract was washed with $H_2O$, dried over anhydrous $MgSO_4$, and filtrated. The filtrate was evaporated to dryness and the residue was purified by column chromatography on silica gel (dichloromethane/methanol=100:1) to obtain the compound (1.93 g, 88%).

Yield:

7 g (88%)

NMR:

$^1$H NMR (400 MHz, $CDCl_3$) δ 8.01-7.84 (m, 2H), 6.96-6.85 (m, 2H), 4.29 (q, J=7.1 Hz, 2H), 4.12 (dd, J=5.4, 4.3 Hz, 2H), 3.82 (dd, J=5.4, 4.2 Hz, 2H), 3.71-3.56 (m, 10H), 3.51-3.45 (m, 2H), 3.32 (s, 3H), 1.32 (t, J=7.1 Hz, 3H).

$^{13}$C{$^1$H} NMR (101 MHz, CDCl3) δ 166.29 (s), 162.47 (s), 131.45 (s), 123.01 (s), 114.11 (s), 71.90 (s), 70.84 (s), 70.60 (s), 70.59 (s), 70.58 (s), 70.48 (s), 69.51 (s), 67.54 (s), 60.57 (s), 58.98 (s), 14.35 (s).

MS(+):

[M+Na$^+$]$^+$=calc. 379.1727, found 379.1743.

Synthesis of 4-PEG4-benzoic Acid

Procedure:

(JACS, 2007, 129, 13364) A mixture of compound ethyl 4-(2,5,8,11-tetraoxatridecan-13-yloxy)benzoate (7 g, 19.6 mmol), and KOH (2.3 g, 41.24 mmol) in 200 mL of EtOH/$H_2O$ (1:1 v/v) was refluxed overnight. After cooling down, the mixture was neutralized with HCl (2N). The resulting mixture was extracted with EtOAc and evaporated to dryness. The resulting white solid was recrystallized in EtOAc/hexane.

Yield:

5.3 g (85%)

NMR:

$^1$H NMR (300 MHz, $CDCl_3$) δ 11.17 (s, 1H), 8.14-7.89 (m, 2H), 7.03-6.75 (m, 2H), 4.29-4.02 (m, 2H), 3.92-3.81 (m, 2H), 3.78-3.57 (m, 10H), 3.57-3.46 (m, 2H), 3.35 (s, 3H).

$^{13}$C{$^1$H} NMR (75 MHz, $CDCl_3$) δ 171.46 (s), 163.24 (s), 132.30 (s), 121.98 (s), 114.33 (s), 71.96 (s), 70.91 (s), 70.67 (s), 70.66 (s), 70.64 (s), 70.54 (s), 69.55 (s), 67.66 (s), 59.08 (s).

MS(−):

[M−H]$^−$=calc. 327.1438, found 327.1456.

Synthesis of N-biphenyl-2-yl-4-(2-{2-[2-(2-methoxy-ethoxy)-ethoxy]-ethoxy}-ethoxy)-benzamide Procedure:

To a solution of 4-(2,5,8,11-tetraoxatridecan-13-yloxy) benzoic acid (3 g, 9.14 mmol), 0.2 mL of DMF in 30 mL dry DCM at 0° C., oxalyl chloride (1.05 mL, 12.34 mmol) was added. The reaction mixture was stirred at 0° C. for 1 h. The solution was concentrated to dryness. The oily residue was used without further purification in the next step.

A solution of 2-phenylaniline (1.6 g), pyridine (2.4 mL) in chloroform (80 mL) under inert atmosphere was cooled down to 0° C. (phenyl-4-(2,5,8,11-tetraoxatridecan-13-yloxy)benzoyl chloride (3.1 g, 9.14 mmol) in 20 mL was slowly added to the solution and the final mixture allowed to reach room temperature. The solution was refluxed for 2 h and stirred overnight at room temperature. The reaction mixture was extracted with HCl (1 M, 2×100 mL), $NaHCO_3$ (100 mL) and water (50 mL). The organic phase was dried with $MgSO_4$ and purified by chromatography in silica gel (EtOAc/hexane).

Yield:

4.1 (90%)

NMR:

$^1$H NMR (400 MHz, CDCl$_3$) δ 8.49 (dd, J=8.3, 0.9 Hz, 1H), 7.94 (s, 1H), 7.61-7.35 (m, 9H), 7.33-7.25 (m, 1H), 7.19 (m, 1H), 6.91-6.84 (m, 2H), 4.16-4.10 (m, 2H), 3.85 (m, 2H), 3.77-3.58 (m, 10H), 3.56-3.49 (m, 2H), 3.36 (s, 3H).

$^{13}$C{$^1$H} NMR (101 MHz, CDCl3) δ 164.56 (s), 161.65 (s), 138.18 (s), 135.12 (s), 132.32 (s), 129.97 (s), 129.39 (s), 129.22 (s), 128.66 (s), 128.57 (s), 128.16 (s), 127.13 (s), 124.18 (s), 121.23 (s), 114.57 (s), 71.95 (s), 70.89 (s), 70.64 (s), 70.63 (s), 70.54 (s), 69.54 (s), 67.63 (s), 59.04 (s), 53.51 (s).

MS(+)

[M+H]$^+$=calc. 480.2386 found. 480.2383; [M+Na]$^+$=calc. 502.2200, found 502.2204.

Synthesis of 6-[4-(2-{2-[2-(2-methoxy-ethoxy)-ethoxy]-ethoxy}-ethoxy)-phenyl]-phenanthridine Procedure:

N-Biphenyl-2-yl-4-(2-{2-[2-(2-methoxy-ethoxy)-ethoxy]-ethoxy}-ethoxy)-benzamide (4 g, 8.34 mmol), POCl$_3$ (10 ml) in 10 ml toluene were refluxed for 20 h. The mixture was cooled down to room temperature, and 100 ml of dichloromethane were added. The solution was poured into ice and the mixture neutralized with NH$_4$OH (20%). The organic phase was extracted and washed successively with destilled water and brine, and dried over MgSO$_4$. The resulting solution was purified by flash chromatography (silica gel, in ethyl acetate/hexane 1:1, R$_f$=0.14).

Yield:

1 g (25%)

NMR:

$^1$H NMR (300 MHz, CDCl$_3$) δ 8.68 (d, J=8.3 Hz, 1H), 8.59 (dd, J=8.1, 1.4 Hz, 1H), 8.23 (dd, J=8.1, 1.1 Hz, 1H), 8.15 (dd, J=8.3, 0.7 Hz, 1H), 7.84 (ddd, J=8.3, 7.1, 1.3 Hz, 1H), 7.79-7.57 (m, 5H), 7.15-7.03 (m, 2H), 4.29-4.19 (m, 2H), 3.93-3.90 (m, 2H), 3.80-3.60 (m, 12H), 3.59-3.49 (m, 2H), 3.37 (s, 3H).

$^{13}$C{$^1$H} NMR (75 MHz, CDCl$_3$) δ 160.92 (s), 159.45 (s), 143.84 (s), 133.59 (s), 131.26 (s), 130.61 (s), 130.26 (s), 129.05 (s), 128.90 (s), 127.19 (s), 126.85 (s), 125.39 (s), 123.70 (s), 122.29 (s), 122.01 (s), 114.68 (s), 72.02 (s), 70.97 (s), 70.74 (s), 70.72 (s), 70.69, 70.62 (s), 69.80 (s), 67.68 (s), 59.15 (s).

MS (+),

[M+H]$^+$ calc=462.2280, found 462.2275.

Example 2

General Procedure for the Synthesis of Chloro-Cross-Linked Dimer Complex

The general procedure was published by Nonoyama, M., J. Organomet. Chem. 86 (1975) 263-267.

The iridium dimers were synthesized as follow: IrCl$_3$.3H$_2$O and 2.5 equiv of 6-phenylphenanthridine were heated at 120° C. for 18 h under nitrogen in 2-ethoxyethanol/water mixture (3:1, v/v). After being cooled to room temperature the precipitate was filtered off and successively washed with methanol and Et$_2$O, dried to afford the desired dimer.

Example 2.1

Bis-Iridium Complex with 6 [4 (2 {2 [2 (2 methoxy-ethoxy)-ethoxy]-ethoxy}-ethoxy)-phenyl]-phenanthridine

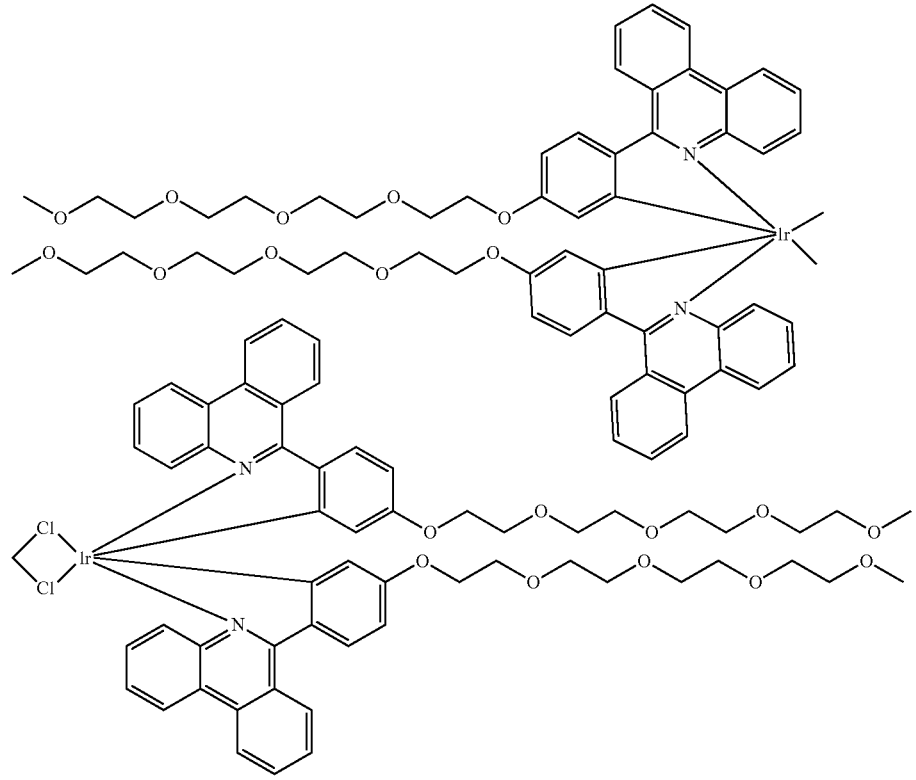

A mixture of 6-[4-(2-{2-[2-(2-methoxy-ethoxy)-ethoxy]-ethoxy}-ethoxy)-phenyl]-phenanthridine (1 g, 2.16 mmol), IrCl$_3$.3H$_2$O (346 mg, 0.98 mmol) in 16 ml of 2-EtOEtOH: H$_2$O (12:4) was refluxed overnight under nitrogen atmosphere. The reaction mixture was cooled down to room temperature and 60 ml of water were added to obtain an oily precipitate. The supernatant was discarded and 50 ml of water were added to the residue. The mixture was stirred for 1 h to obtain a red-brownish precipitate. The solid was filtrated and washed with water (50 ml) and Et$_2$O (30 ml). The brown solid was dissolved in the smaller amount of dichloromethane and precipitated upon addition of Et$_2$O. It was used in the next step without further purification.

Yield:

550 mg (50%)

NMR:

$^1$H NMR (300 MHz, CDCl$_3$) δ 8.74 (d, J=8.1 Hz, 4H), 8.36 (dd, J=8.0, 5.2 Hz, 8H), 7.90 (dd, J=14.7, 7.7 Hz, 8H), 7.81 (d, J=9.0 Hz, 4H), 7.79-7.67 (m, 4H), 6.78-6.65 (m, 4H), 6.32 (dd, J=8.8, 2.5 Hz, 4H), 5.89-5.83 (m, 4H), 5.28 (d, J=2.5 Hz, 4H), 3.67-3.10 (m, 100H, PEG Chain, contains some impurities)

MS(ESI-MS(+)):

[M+2Na$^+$]$^{2+}$ calc. 1171.3463, found 1171.3473; [(C^N)$_2$Ir]$^+$=calc. 1113.3877, found 1113.3892.

Example 3

Synthesis of Sulfonate Substituted Phenylphenanthridines and their Use in Building Bis-Phenylphenanthridine Complexes Example 3.1

Synthesis of 3-(4-phenanthridin-6-yl-phenoxy)-propane-1-sulfonate Caesium Salt

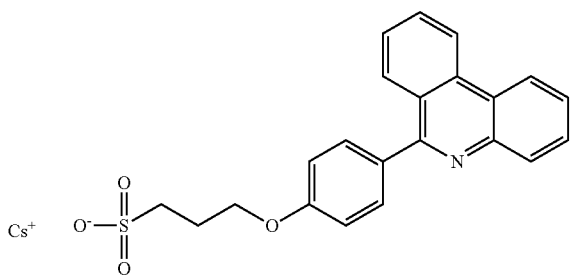

6-(4-Methoxyphenyl)phenanthridine was prepared by cyclisation of the N-(biphenyl-2-yl)-4-methoxybenzamide (2 g, 6.59 mmol) following the procedure as described above. The compound was purified by chromatography in dichloromethane/hexane (gradient 1:5 to 1:1). Yield: 87%.

NMR:

$^1$H NMR (300 MHz, DMSO) δ 8.94 (d, J=8.2 Hz, 1H), 8.84 (dd, J=8.2, 1.2 Hz, 1H), 8.18-8.05 (m, 2H), 7.97 (ddd, J=8.3, 7.1, 1.3 Hz, 1H), 7.86-7.62 (m, 5H), 7.23-7.07 (m, 2H), 3.88 (s, 3H).

$^1$H NMR (300 MHz, CDCl$_3$) δ 8.70 (d, J=8.3 Hz, 1H), 8.61 (dd, J=8.1, 1.3 Hz, 1H), 8.28 (d, J=8.0 Hz, 1H), 8.18 (dd, J=8.3, 0.7 Hz, 1H), 7.86 (ddd, J=8.3, 7.1, 1.3 Hz, 1H), 7.81-7.56 (m, 5H), 7.18-7.02 (m, 2H), 3.92 (s, 3H).

$^{13}$C NMR (75 MHz, CDCl$_3$) δ 160.95 (s), 160.33 (s), 143.72 (s), 133.67 (s), 132.12 (s), 131.36 (s), 130.71 (s), 130.20 (s), 129.13 (s), 128.97 (s), 127.23 (s), 126.92 (s), 125.40 (s), 123.73 (s), 122.33 (s), 122.03 (s), 114.03 (s), 55.57 (s).

MS [ESI-MS (+)]:

[M+H$^+$]$^-$ found 286.1231, calc. 286.1226.

4-Phenanthridin-6-yl-phenol: Deprotection of the 6-(4-methoxyphenyl)phenanthridine was achieved by using HBr. A suspension of 6-(4-methoxyphenyl)phenanthridine (1 g, 3.5 mmol) in 15 mL (HBr, 47%) was refluxed at 100° C. for 12 h. The mixture was cooled down to room temperature, poured into ice-water and neutralized with Na$_2$CO$_3$. The resulting precipitate was filtered off and washed with water and Et$_2$O. The solid was purified by chromatography column using dichloromethane/MeOH. Yield: 90%.

NMR:

$^1$H NMR (300 MHz, DMSO) δ 9.84 (s, 1H), 8.92 (d, J=8.2 Hz, 1H), 8.82 (dd, J=8.2, 1.2 Hz, 1H), 8.20-8.11 (m, 1H), 8.08 (dd, J=8.1, 1.2 Hz, 1H), 8.02-7.88 (m, 1H), 7.84-7.64 (m, 3H), 7.64-7.49 (m, 2H), 7.06-6.89 (m, 2H).

MS [ESI-MS (−)]:

[M−H$^+$]$^-$ found 270.0922, calc. 270.0924.

To a solution of 4-(phenanthridin-6-yl)phenol (320 mg, 1.18 mmol) in DMF (4 ml), Cs$_2$CO$_3$ (482.2 mg, 1.48 mmol) and 1,3-propylsultone (159 mg, 1.30 mmol) were added. The reaction mixture was stirred overnight at room temperature. The reaction mixture was concentrated to dryness and the residue was purified by chromatography column (silica) using dichloromethane/MeOH (gradient 10:1 to 5:1). Yield: 72%

NMR:

$^1$H NMR (300 MHz, DMSO-d$_6$) δ 8.98-8.87 (m, 1H), 8.83 (dd, J=7.9, 1.6 Hz, 1H), 8.12 (m, 2H), 7.97 (ddd, J=8.3, 7.0, 1.3 Hz, 1H), 7.85-7.69 (m, 3H), 7.67 (d, J=8.6 Hz, 2H), 7.14 (d, J=8.7 Hz, 2H), 4.19 (t, J=6.5 Hz, 2H), 2.64-2.57 (m, 2H), 2.15-1.97 (m, 2H).

MS [EI-MS (−)]:

[M−Cs$^+$]$^-$ calc 392.0956. found 392.0962.

Example 3.2

Synthesis of Bis-Iridium Complex with 3-(4-phenanthridin-6-yl-phenoxy)-propane-1-sulfonate Caesium Salt

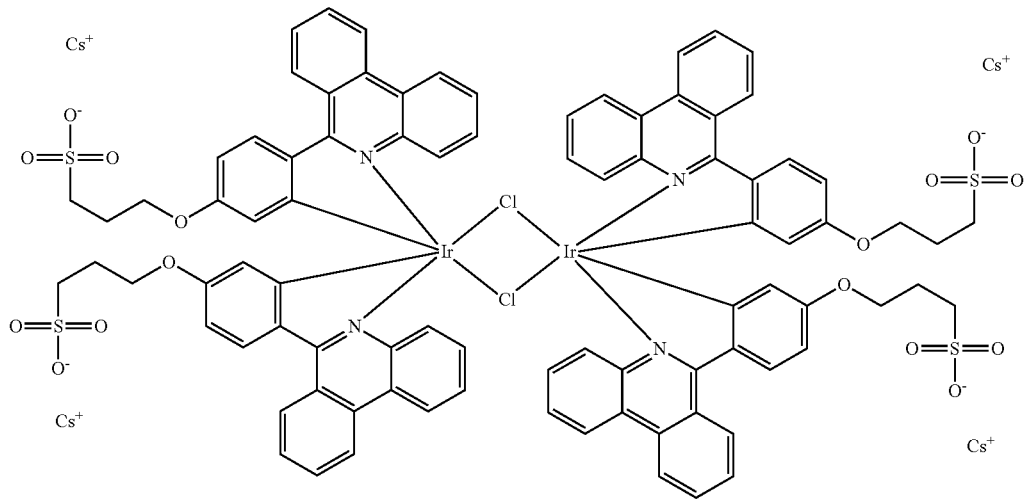

A mixture of the ligand caesium 3-(4-(phenanthridin-6-yl)phenoxy)propane-1-sulfonate (500 mg, 0.92 mmol) and IrCl$_3$ (159.5 mg, 0.45 mmol) in 2-ethoxyethanol:water (3:1, 16 ml) mixture, was refluxed under nitrogen atmosphere for 36 h. The reaction mixture was filtered, and the filtrate was concentrated to dryness. The residue was used for the synthesis of iridium monomer complexes without further purification.

MS [ESI-MS(−)]:
[Ir(C^N)$_2$-2Cs$^+$]$^−$ calc 975.13858, found 975.13882.

Example 3.3

Synthesis of (4-phenanthridin-6-yl-phenyl)-methanesulfonic Acid

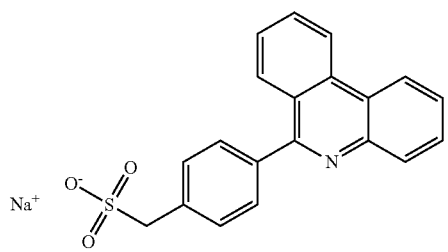 [SMILES: [Na+] ; O=S(=O)([O-])Cc1ccc(-c2nc3ccccc3c3ccccc23)cc1]

6-(4-Chloromethyl-phenyl)-phenanthridine

4-Chloromethyl-benzoylchloride (2.5 g, 13.2 mmol) and 2-amino-biphenyl (1.95 g, 11.5 mmol) were dissolved in DCM (50 mL) and stirred at 45° C. for 4 h and subsequently for another 16 h at RT under argon. To the mixture pyridine (2.4 mL) was added and the organic layer was washed with water (2×50 mL). The organic layer was next dried over Na$_2$SO$_4$, filtered and evaporated, yielding 3.78 g of N-biphenyl-2-yl-4-chloromethyl-benzamide.

MS [ESI-MS(+)]:
calcd for C$_{20}$H$_{17}$ClNO: 322.1[M+H]$^+$; found 322.3.

N-Biphenyl-2-yl-4-chloromethyl-benzamide, POCl$_3$ (20 mL) and toluene (40 mL) were combined and stirred at 120° C. for 16 h. The reaction mixture was dried by evaporation and the residue taken up in etylacetate (100 mL), the organic layer was then washed with NaHCO$_3$ (sat.) (2×50 mL). The organic layer was dried over Na$_2$SO$_4$, filtered and evaporated to yield 1.96 g of 6-(4-chloromethyl-phenyl)-phenanthridine.

MS [ESI-MS(+)]:
calcd for C$_{20}$H$_{15}$ClN: 304.1[M+H]$^+$; found 304.4.

(4-Phenanthridin-6-yl-phenyl)-methanesulfonate sodium salt: 6-(4-chloromethyl-phenyl)-phenanthridine (1.3 g) and sodium sulfite (5 g) were dissolved in a mixture of H$_2$O/MeOH (35/16 mL) and stirred at 100° C. for 11 h under argon atmosphere. The reaction mixture was filtered and the volume reduced to 10 mL under reduced pressure. The product was subsequently precipitated by the addition of 30 mL MeOH. The product was next filtered off and washed with a mixture of MeOH/H$_2$O (3/1, v/v). The RM was next dried under reduced pressure to yield 1.0 g of (4-phenanthridin-6-yl-phenyl)-methanesulfonate sodium salt.

MS [ESI-MS(+)]:
calcd for C$_{20}$H$_{16}$NO$_3$: 350.1[M+H]$^+$; found 350.4.

Example 3.4

Synthesis of Bis-Iridium Complex with (4-phenanthridin-6-yl-phenyl)-methanesulfonic Acid

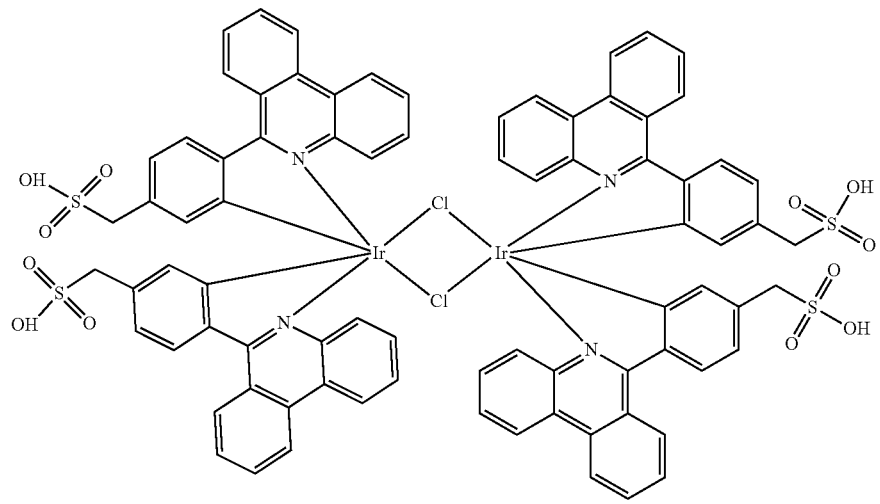

(4-Phenanthridin-6-yl-phenyl)-methanesulfonic acid (50 mg) and IrCl$_3$ (30 mg) were dissolved in a mixture of 2-ethoxyethanol and water (3:1, v/v), to which DIPEA (25 µL) was added. The reaction mixture was stirred at 110° C. overnight under Ar. Subsequently, the mixture was cooled down to room temperature and filtered over a nitrocellulose (0.45 µm) filter, yielding a bright red solution. The volatiles were evaporated and the product purified by HPLC.

MS [ESI-MS(+)]:

Calcd. for (M−2H$^+$)$^−$: C$_{40}$H$_{26}$IrN$_2$O$_6$S$_2$ 887.1. Found: 887.1 (=observed fragment of one iridium ion with two ligands).

Example 3.5

Synthesis of the Sodium Salt of (6-phenyl-phenanthridin-9-yl)-methanesulfonate

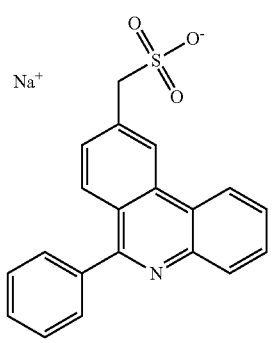 [SMILES: O=S(=O)([O-])Cc1ccc2c(-c3ccccc3)nc3ccccc3c2c1 ; [Na+]]

Step 1: m-tolylboronic acid (10 g, 73.55 mmol), 2-bromoaniline (15.1 g, 88.26 mmol), KF (10 g, 172 mmol), tricyclohexylphosphine (1 g, 3.56 mmol), and Pd(OAc)$_2$ (260 mg, 1.15 mmol) were suspended/dissolved in dry THF (100 mL) under Ar atmosphere and stirred overnight at 80° C.

Subsequently, the RM was taken up in EtOAc and washed with water (twice 100 mL). The organic layer was dried over Na$_2$SO$_4$, filtered and the volatiles were evaporated, yielding a dark yellow oil. The product was next purified on a silica column, using a system of 5 to 15% EtOAc in petroleum ether.

Yield: 8 g (60%)

MS [ESI-MS(+)]:

Calcd. for (M+H$^+$): C$_{13}$H$_{14}$N, 184.1. Found: 184.2.

Step 2: (8 g, 43.48 mmol) product of step 1 and benzoylchloride (5 mL 43.48 mmol) were reacted in dry DCM at room temperature under Ar atmosphere for 2 h. The volatiles were evaporated and the residue was taken up in EtOAc and washed with NaHCO$_3$ sat. (twice 50 mL) and once with brine. The organic layer was dried over Na$_2$SO$_4$, filtered and the volatiles were evaporated, yielding dark yellow oil. The product was next purified on a silica column, using a system of 5 to 15% EtOAc in petroleum ether. This yielded two products that could not be separated using silica chromatography.

Approximate yield: 12 g (~90%)

MS [ESI-MS(+)]:

Calcd. for (M+H$^+$): C$_{20}$H$_{18}$NO 288.1 Found: 288.2.

Step 3: The crude product of step 2 (12 g, 45 mmol) was dissolved in toluene (100 mL), to which POCl$_3$ (80 mL) was added. The mixture was next stirred overnight, at 120° C., under Ar atmosphere. Subsequently, the volatiles were evaporated and the residue was taken up in EtOAc and washed with NaHCO$_3$ sat. (twice 100 mL) and once with brine. The organic layer was dried over Na$_2$SO$_4$, filtered and the volatiles were evaporated, yielding dark yellow oil. The product was next purified on a silica column, using a system of 5 to 15% EtOAc in petroleum ether. This again yielded two products that however were separated nicely using 2% MeOH in DCM.

Approximate yield: 8 g (66%)

MS [ESI-MS(+)]:

Calcd. for (M+H$^+$): C$_{20}$H$_{16}$N: 270.1 Found: 270.2.

Step 4: The product of step 3 (500 mg, 1.8 mmol) was dissolved in THF (5 mL) and cooled to −78° C. under Ar atmosphere. Next, LDA (2.5 mL) was added and the mixture was stirred for 15 min at −78° C. Subsequently, chlorotrimethylsilane (0.5 mL) was added and the mixture was again stirred for another 15 min., after which the reaction was quenched with EtOH (0.6 mL). The mixture was taken up in EtOAc (50 mL) and washed with NaHCO₃ sat. (twice 20 mL) and once with brine (20 mL). The organic layer was dried over Na₂SO₄, filtered and the volatiles were evaporated, yielding dark yellow oil.

Approximate yield: 200 mg (40%)

MS [ESI-MS(+)]:

Calcd. for (M+H⁺): $C_{23}H_{23}NSi$: 342.2 Found: 342.2.

Step 5: The crude product of step 5, (250 mg, 0.73 mmol), CsF (540 mg, 3.5 mmol), $C_2Cl_6$ (840 mg, 3.5 mmol) were dissolved/suspended in CH₃CN (5 mL) and stirred at 70° C. for 2 h under Ar atmosphere. The mixture was taken up in EtOAc (50 mL) and washed with water (20 mL) and once with brine (20 mL). The organic layer was dried over Na₂SO₄, filtered and the volatiles were evaporated, yielding pale yellow solid.

MS [ESI-MS(+)]:

Calcd. for (M+H⁺): $C_{20}H_{15}ClN$: 304.1 Found: 304.1.

Step 6: The crude product of step 5 (250 mg, 0.8 mmol) and Na₂SO₃ (200 mg, 1.5 mmol) were dissolved in a mixture of MeOH/water (10 mL, 1:1, v/v) and stirred while refluxing for 10 h. Subsequently, the volatiles were evaporated and the residue was taken up in EtOAc and water. The water layer containing the product was dried and further purified on a diaion column (2 to 20% acetone in water, eluting the product with ~15% acetone). The product was next further purified using HPLC on a preparative Vydac C-18 column in a system of 2 to 50% CH₃CN in water.

MS [ESI-MS(+)]:

Calcd. for (M+H⁺): $C_{20}H_{15}ClN$: 350.1 Found: 350.1.

Example 3.6

The Synthesis of Disodium Salt of (6-phenyl-2-sulfomethyl-phenanthridin-9-yl)-methanesulfonic Acid

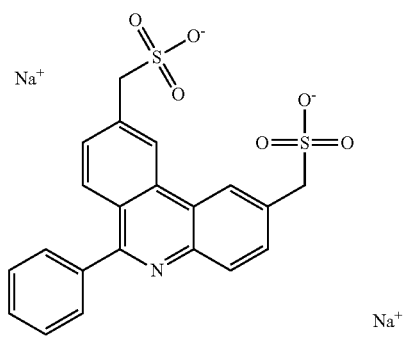 [SMILES: O=S(=O)([O-])Cc1ccc2nc(-c3ccccc3)c3ccc(CS(=O)(=O)[O-])cc3c2c1 ; [Na+] ; [Na+]]

The synthesis of disodium salt of (6-phenyl-2-sulfomethyl-phenanthridin-9-yl)-methanesulfonic acid was carried out according to the procedure described in example 3.4 using the appropriate starting materials and stoichiometries.

The invention claimed is:

1. An iridium-based compound of Formula I

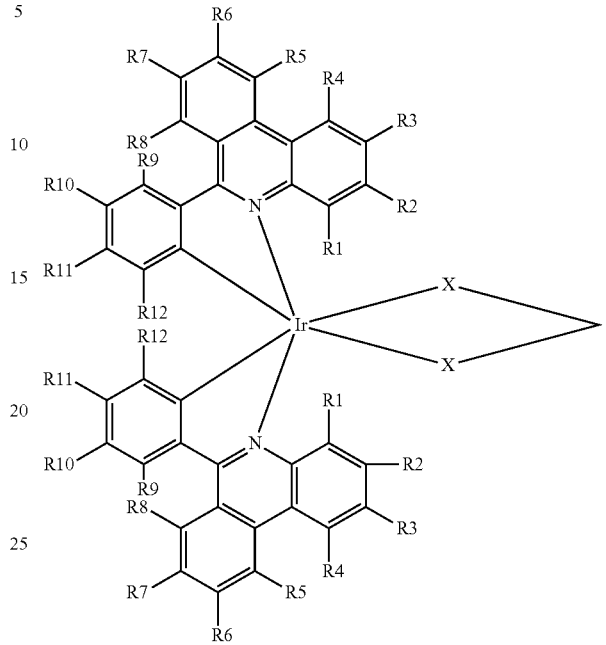

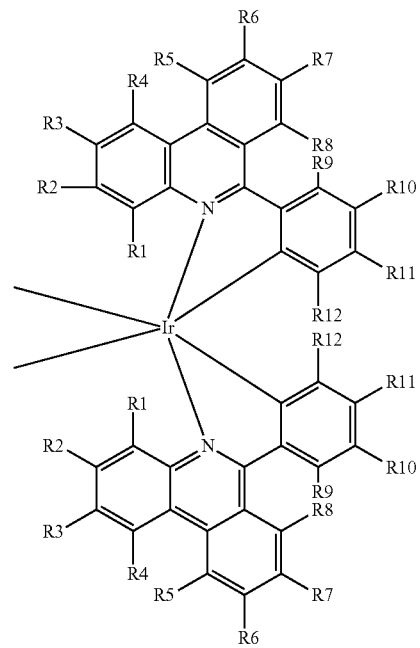

wherein the compound of Formula I is symmetrical, wherein each X is independently chloro, bromo, iodo, wherein the phenyl-phenanthridine residues comprised in Formula I are selected from one or more of the below given substituted phenyl-phenanthridines:

35
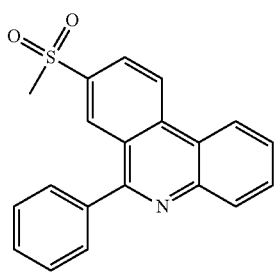
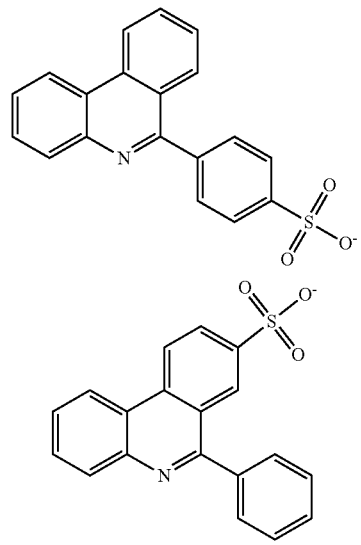
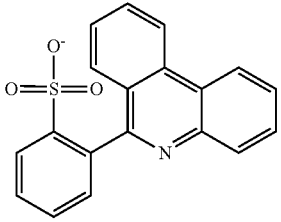
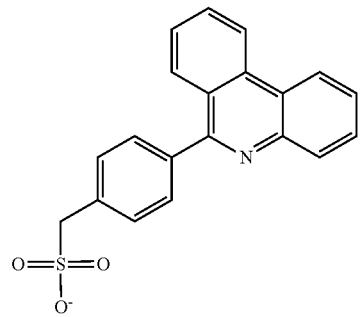
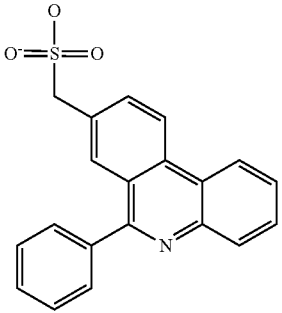
36
-continued
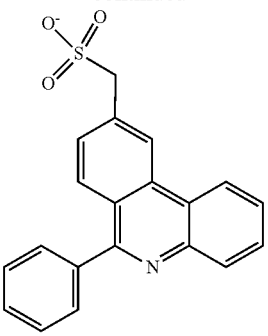
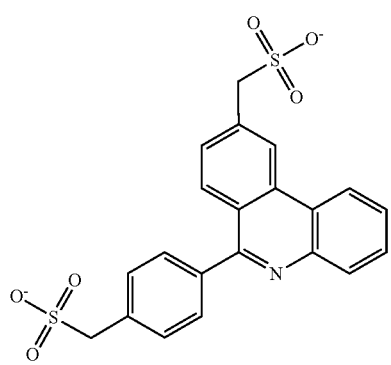
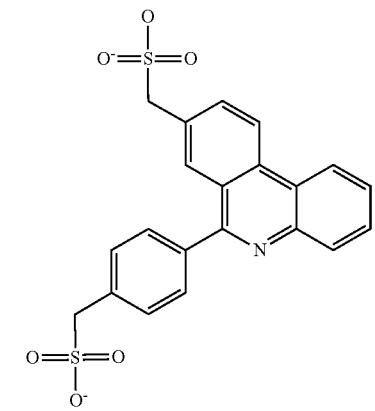
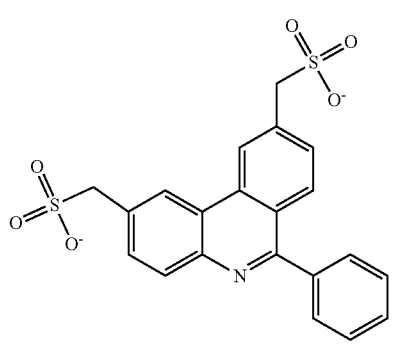

-continued
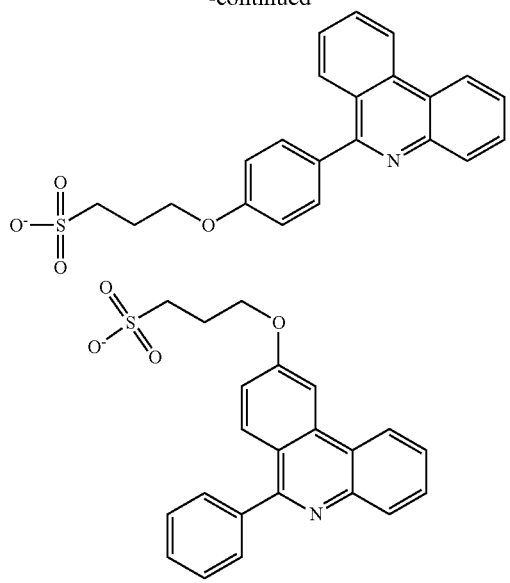
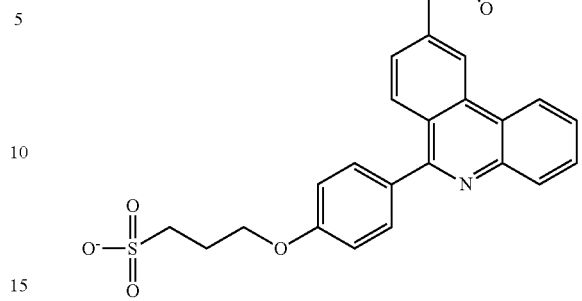
or a salt thereof.
2. A method for producing an electrochemiluminescent label, the method comprising the steps of incubating an iridium dimer complex according to claim 1 with a third ligand in an organic solvent under inert gas atmosphere.
* * * * *